US008712539B2

(12) United States Patent
Goetz et al.

(10) Patent No.: US 8,712,539 B2
(45) Date of Patent: Apr. 29, 2014

(54) RULE-BASED STIMULATION PROGRAM SEARCH

(75) Inventors: Steven M. Goetz, Brooklyn Center, MN (US); Donald R. Johnson, Lino Lakes, MN (US); Andrew H. Houchins, Lino Lakes, MN (US); Jeffrey T. Keacher, St. Paul, MN (US); Theodore J. Stone, St. Louis Park, MN (US); Kenneth T. Heruth, Edina, MN (US); Gary W. King, Fridley, MN (US); Roy L. Testerman, New Hope, MN (US)

(73) Assignee: Medtronic, Inc., Minneapolis, MN (US)

( * ) Notice: Subject to any disclaimer, the term of this patent is extended or adjusted under 35 U.S.C. 154(b) by 1769 days.

(21) Appl. No.: 11/402,657

(22) Filed: Apr. 12, 2006

(65) Prior Publication Data

US 2007/0245318 A1 Oct. 18, 2007

(51) Int. Cl.
*A61N 1/372* (2006.01)

(52) U.S. Cl.
USPC ............................................. 607/59; 607/30

(58) Field of Classification Search
USPC ....................................... 607/30, 31, 59, 117
See application file for complete search history.

(56) References Cited

U.S. PATENT DOCUMENTS

| | | | |
|---|---|---|---|
| 4,515,158 | A | 5/1985 | Patrick et al. |
| 4,549,548 | A | 10/1985 | Wittkampf et al. |
| 5,033,469 | A | 7/1991 | Brodard |
| 5,775,331 | A | 7/1998 | Raymond et al. |
| 5,893,883 | A | 4/1999 | Torgerson et al. |
| 5,938,690 | A | 8/1999 | Law et al. |
| 6,044,303 | A | 3/2000 | Agarwala et al. |
| 6,052,624 | A | 4/2000 | Mann |
| 6,393,325 | B1 | 5/2002 | Mann et al. |
| 6,440,090 | B1 | 8/2002 | Schallhorn |

(Continued)

FOREIGN PATENT DOCUMENTS

| | | |
|---|---|---|
| EP | 0 730 882 | 9/1996 |
| EP | 1 249 254 | 10/2002 |

(Continued)

OTHER PUBLICATIONS

U.S. Appl. No. 11/402,652, filed Apr. 12, 2006 entitled Autogeneration of Neurostimulation Therapy Program Groups by Jeffrey T. Keacher et al.

(Continued)

*Primary Examiner* — Joseph Dietrich
(74) *Attorney, Agent, or Firm* — Shumaker & Sieffert, P.A.

(57) ABSTRACT

Techniques that involve application of one or more rules to a "parent" program to generate a plurality of different "child" programs are described. Each of the rules may define a respective electrode configuration modification, and each child program may be a variation of the parent based on a modification of the electrode configuration of the parent according to one of the rules. The systems or devices may generate further generations of child programs from a previous generation child program using the same one or more rules. The child programs may be provided to a user, so that the user may test the efficacy of the new programs, assisting the user in identifying desirable programs. The child programs may be relatively minor variations of the parent program, and the user may "fine tune" a generally desirable parent program by testing the child programs.

47 Claims, 11 Drawing Sheets

(56) References Cited

U.S. PATENT DOCUMENTS

| | | | |
|---|---|---|---|
| 6,473,653 | B1 | 10/2002 | Schallhorn et al. |
| 6,480,743 | B1 | 11/2002 | Kirkpatrick et al. |
| 6,587,724 | B2 | 7/2003 | Mann |
| 2002/0035384 | A1 | 3/2002 | Fox et al. |
| 2002/0116036 | A1 | 8/2002 | Daignault, Jr. et al. |
| 2002/0169484 | A1 | 11/2002 | Mathis et al. |
| 2003/0004549 | A1 | 1/2003 | Hill et al. |
| 2003/0036783 | A1 | 2/2003 | Bauhahn et al. |
| 2004/0041352 | A1 | 3/2004 | Hohe et al. |
| 2004/0158298 | A1 | 8/2004 | Gliner et al. |
| 2004/0181262 | A1 | 9/2004 | Bauhahn |
| 2004/0215288 | A1 | 10/2004 | Lee et al. |
| 2004/0267330 | A1 | 12/2004 | Lee et al. |
| 2005/0060009 | A1 | 3/2005 | Goetz |

FOREIGN PATENT DOCUMENTS

| | | |
|---|---|---|
| EP | 1 304 137 | 4/2003 |
| WO | WO 01/83028 | 11/2001 |
| WO | WO 01/93953 | 12/2001 |
| WO | WO 02/09808 | 2/2002 |
| WO | WO 2004/041352 | 5/2004 |

OTHER PUBLICATIONS

Notification of Transmittal of the International Preliminary Report on Patentability dated Mar. 12, 2008 for corresponding PCT Application Serial No. PCT/US2007/002274 (13 pgs).

Litt et al., "Translating Seizure Detection, Prediction and Brain Stimulation Into Implantable Devices for Epilepsy," Proceedings of the 1st International IEEE EMBS, Conference on Neural Engineering Capri Island, Italy, Mar. 20-22, 2003, pp. 485-488.

D'Alessandro et al., "A Genetic Approach to Selecting the Optimal Feature for Epileptic Seizure Prediction," 2001 Proceedings of the 23rd Annual EMBS International Conference, Istanbul, Turkey, Oct. 25-28, 2001, pp. 1703-1706.

International Search Report and Written Opinion dated Jun. 20, 2007 for corresponding PCT Application Serial No. PCT/US2007/002274 (11 pgs).

Final Office Action for U.S. Appl. No. 13/330,016, dated May 17, 2013, 9 pages.

Response to Final Office Action dated May 17, 2013, from U.S. Appl. No. 13/330,016, filed Jul. 17, 2013, 13 pages.

Notice of Allowance dated Sep. 6, 2013, from U.S. Appl. No. 13/330,016, 10 pages.

Response to office action for U.S. Appl. No. 13/330,016, filed Jun. 25, 2012, 17 pages.

Office action for U.S. Appl. No. 13/330,016, dated Mar. 30, 2012, 8 pages.

RULE-BASED STIMULATION PROGRAM SEARCH

TECHNICAL FIELD

The invention relates to medical devices and, more particularly, to devices that deliver stimulation.

BACKGROUND

Implantable medical devices may be used to deliver neurostimulation therapy to patients to treat a variety of symptoms or conditions such as chronic pain, tremor, Parkinson's disease, epilepsy, urinary or fecal incontinence, sexual dysfunction, obesity, or gastroparesis. An implantable medical device may deliver neurostimulation therapy via leads that include electrodes located proximate to the spinal cord, pelvic nerves, stomach, peripheral nervous system, or within the brain of a patient. In general, the implantable medical device delivers neurostimulation therapy in the form of electrical pulses.

A clinician selects values for a number of programmable parameters in order to define the neurostimulation therapy to be delivered to a patient. For example, the clinician selects an amplitude, which may be a current or voltage amplitude, and pulse width for a stimulation waveform to be delivered to the patient, as well as a rate at which the pulses are to be delivered to the patient. The clinician may also select particular electrodes within an electrode set implanted within the patient to be used to deliver the pulses, and the polarities of the selected electrodes. A group of parameter values may be referred to as a program in the sense that they drive the neurostimulation therapy to be delivered to the patient. The selected electrodes and polarities may be referred to as an electrode configuration for the program.

The process of selecting values for the parameters can be time consuming, and may require a great deal of trial and error before one or more preferred stimulation programs are discovered. As a portion of the overall parameter selection process, the process of selecting electrode configurations can be particularly time-consuming and tedious. The clinician typically needs to test a large number of possible electrode configurations within the electrode set implanted in the patient in order to identify preferred electrode configurations. A "preferred" program or electrode configuration may be a program or electrode configuration that provides a preferable balancing of efficacy, side effects, and stimulation device power consumption.

SUMMARY

In general, the invention is directed to techniques for automatically generating stimulation programs to assist a user, e.g., a clinician or patient, in searching for preferred stimulation programs. More particularly, a system or device according to the invention may apply one or more rules to a "parent" program to generate a plurality of different "child" programs. Each child program may be a variation of the parent based on a modification of the electrode configuration of the parent according to one of the rules. The child programs may be provided to a user, so that the user may test the efficacy of the child programs, assisting the user in identifying desirable programs. The child programs may be relatively minor variations of the parent program, and the user may "fine tune" a generally desirable parent program by testing the child programs.

Each of the rules may define a respective electrode configuration modification based on, as examples, the proximity of active electrodes to each other, the proximity of inactive electrodes to active electrodes, or the number of active electrodes. In general, the rules include at least one of adding an active electrode, removing an active electrode, or changing the location of an active electrode. For example, a rule may specify removal of a cathode that is proximate or adjacent to another cathode, or removal of an anode if there is more than one anode. As other examples, a rule may specify adding an anode or cathode near an existing cathode, or adding an anode near an existing anode. As a further example, a rule may specify moving an anode to a proximate or adjacent inactive electrode. Some of the rules may specify more than one modification, e.g., more than one addition, removal, or movement of an active electrode.

Some embodiments may apply one or more rules to one or more of the child programs to generate second generation child programs, to one or more of the second generation child programs to generate third generation child programs, and so on. In this manner, such embodiments may generate Nth generation child programs as desired by a user. In general, higher generation programs, e.g., higher values of "N," will be less similar to a parent program than lower generation programs. A user may provide an indication of a degree of program similarity, and some embodiments may determine how many generations to generate and which generation to present to the user based on the requested degree of program similarity. In some embodiments, the device or system may select which rules to apply to programs based on user input.

Child programs from one or more selected generations may be presented to the user as a list or sequence. In some embodiments, the user may scroll through the sequence, and select according to which of the child programs in the sequence an implantable medical device (IMD) will deliver stimulation. In other embodiments, the device or system may automatically scroll through the sequence, and control the IMD to deliver stimulation according to each of the child programs. In either case, the user may be provided with an interface to control the direction or speed of scrolling.

Some embodiments may automatically determine an amplitude for a child program based on the amplitude of another child program or a parent program. For example, when scrolling through child programs, a patient or clinician may select one of the child programs, and control the IMD to deliver stimulation according to the selected program. The patient or clinician may adjust the amplitude of the selected program from substantially zero to a desired level. However, adjusting the amplitude of each newly selected child program from substantially zero to a desired amplitude may be tedious and time consuming.

Because the parent and child programs are generally similar, embodiments of the invention may automatically determine an amplitude of a newly selected program based on the final amplitude after adjustment for the parent program or one of the child programs. For example, some embodiments may determine an initial amplitude of a newly selected child program based on the final amplitude of a previously selected child program. The initial amplitude for a current program may be, as examples, a predetermined percentage of the final amplitude of another program, or a predetermined percentage of a mean or median of final amplitudes of a number of previous programs. Other embodiments may determine an initial amplitude for a current program based on perception and/or comfort amplitude thresholds determined for one or more previous programs, or the degree of similarity of the current program to the one or more previous programs. As mentioned above, some embodiments may automatically deliver stimulation according to each child program during scrolling. Such embodiments may deliver stimulation for each child program at an initial amplitude determined based on a final amplitude of one or more previously selected child programs or the parent program.

Child programs may be generated for testing on a patient during an office visit, or at any other time. Generation of child programs according to the invention may be directed by a clinician for the patient, or by the patient. Programming devices, such as clinician or patient programmers, may generate child programs according to the invention. The child program generation techniques of the invention may be utilized throughout the useful lifetime of a stimulation system as the patient's stimulation needs change.

In some embodiments, an IMD may deliver stimulation according to a group of two or more programs at the same time, e.g., by alternating delivery of stimulation according to the programs of the group. In such embodiments, a programming device or IMD may generate child program groups by applying one or more rules to one or more of the constituent programs of a selected parent program group. Such embodiments may be particularly useful for patients away from the clinic, as they may generally be aware of stimulation at the group level, and associate desirable stimulation with a particular group.

In one embodiment, the invention is directed to a method comprising selecting a parent stimulation program, the parent stimulation program including a parent electrode configuration, and applying each of a plurality of rules to the parent electrode configuration. Each of the rules defines a respective electrode configuration modification based on at least one of proximity of active electrodes to each other, proximity of inactive electrodes to active electrodes, or number of active electrodes. The method further comprises generating a plurality of child programs based on the application of the rules to the parent electrode configuration, wherein each of the child programs includes a respective child electrode configuration determined by application of one of the rules to the parent electrode configuration.

In another embodiment, the invention is directed to a system comprising a memory and a processor. The memory stores a plurality of rules, each of the rules defining a respective electrode configuration modification based on at least one of proximity of active electrodes to each other, proximity of inactive electrodes to active electrodes, or number of active electrodes. The processor selects a parent stimulation program, the parent stimulation program including a parent electrode configuration, applies each of the plurality of rules to the parent electrode configuration, and generates a plurality of child programs based on the application of the rules to the parent electrode configuration. Each of the child programs includes a respective child electrode configuration determined by application of one of the rules to the parent electrode configuration.

In an additional embodiment, the invention is directed to a computer readable medium comprising instructions. The instructions cause a programmable processor to select a parent stimulation program, the parent stimulation program including a parent electrode configuration, and apply each of a plurality of rules to the parent electrode configuration. Each of the rules defines a respective electrode configuration modification based on at least one of proximity of active electrodes to each other, proximity of inactive electrodes to active electrodes, or number of active electrodes. The medium further comprises instructions that cause a programmable processor to generate a plurality of child programs based on the application of the rules to the parent electrode configuration, wherein each of the child programs includes a respective child electrode configuration determined by application of one of the rules to the parent electrode configuration.

In another embodiment, the invention is directed to a method comprising selecting a parent program group, the parent program group including a plurality of parent stimulation programs, and each of the parent stimulation programs including a respective one of a plurality of electrode configurations. The method further comprises applying a rule to each of the parent electrode configurations, the rule defining an electrode configuration modification based on at least one of proximity of active electrodes to each other, proximity of inactive electrodes to active electrodes, or number of active electrodes. The method further comprises generating a plurality of child program groups based on the application of the rule to the parent electrode configurations, wherein each of the child program groups includes a respective child stimulation program and corresponding child electrode configuration determined by application of the rule to the parent electrode configuration.

In another embodiment, the invention is directed to a system comprising a memory and a processor. The memory stores a rule that defines an electrode configuration modification based on at least one of proximity of active electrodes to each other, proximity of inactive electrodes to active electrodes, or number of active electrodes. The processor selects a parent program group, the parent program group including a plurality of parent stimulation programs, and each of the parent stimulation programs including a respective one of a plurality of parent electrode configurations. The processor applies the rule to each of the parent electrode configurations, and generates a plurality of child program groups based on the application of the rule to the parent electrode configurations. Each of the child program groups includes a respective child stimulation program and child electrode configuration determined by application of the rule to the parent electrode configuration.

In various embodiments, the invention may provide one or more advantages. For example, generation of child programs may allow more rapid identification of a plurality of potentially efficacious programs than may be possible by manual entry of parameters for each program. Further, generation and testing of child programs may allow a user to "fine tune" a generally desirable parent program.

Because child programs are substantially similar to their parent programs, a patient may be able to safely test child programs without clinical supervision. In some embodiments, a patient may both generate and test child programs outside of the clinic setting. By allowing testing of child programs outside of the clinic, embodiments of the invention may reduce the burdens on the clinic associated with initially programming stimulation for a patient, and adjusting the programming later as symptoms of the patient change.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
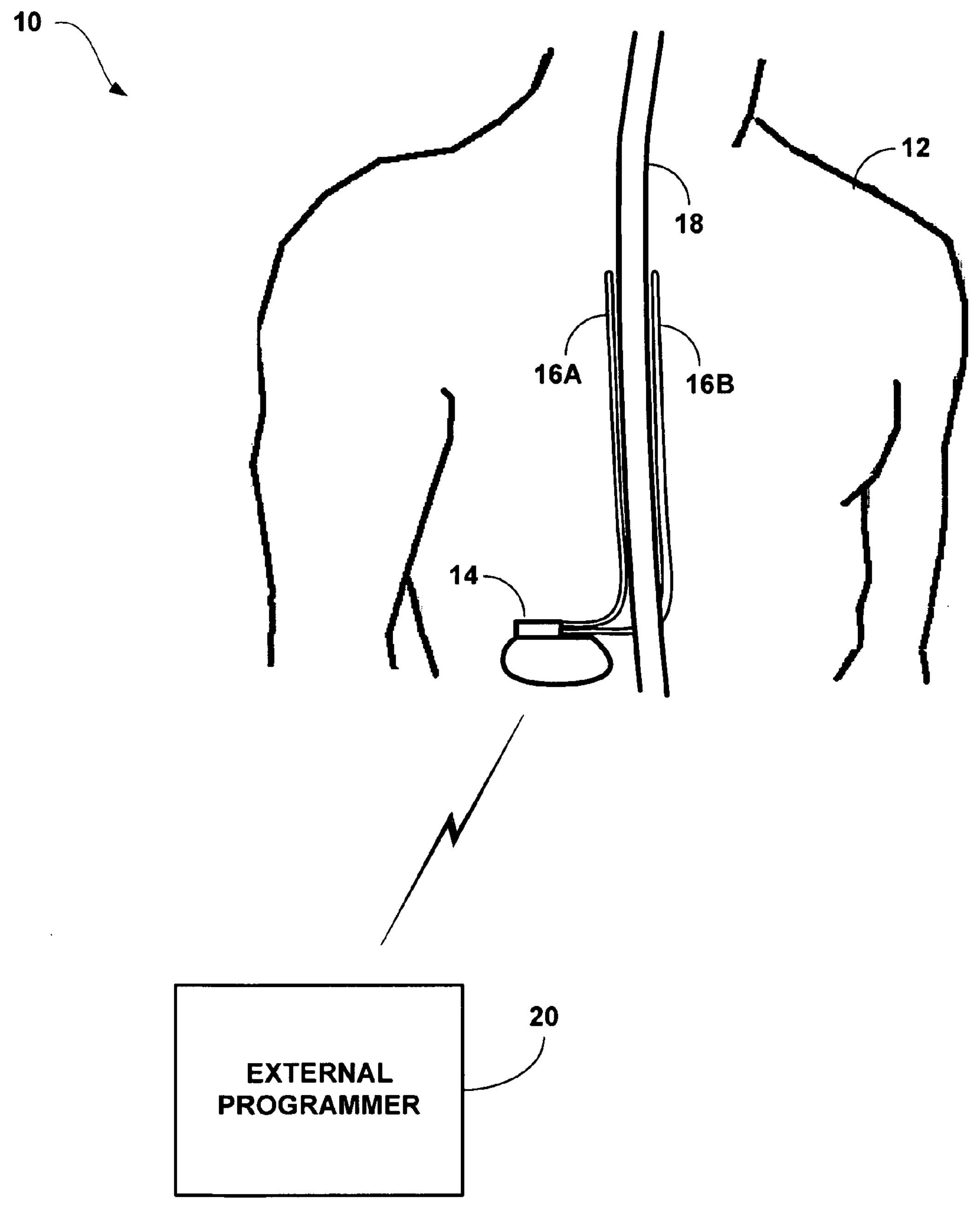
FIG. 1 is a conceptual diagram illustrating an example stimulation system in conjunction with a patient.

FIG. 1 is a conceptual diagram illustrating an example stimulation system 10 in conjunction with a patient 12. System 10 includes an implantable medical device (IMD) 14 that delivers stimulation to patient 12. System 10 also includes a programmer 20, which may communicate with IMD 14 via wireless telemetry. Programmer 20 allows a user, e.g., a clinician or patient 12, to control delivery of stimulation by IMD 14.

In the illustrated embodiment, IMD 14 delivers spinal cord stimulation (SCS) therapy to patient 12 via leads 16A and 16B (collectively "leads 16") implanted proximate to spinal cord 18 of patient 12. SCS therapy may be used, for example, to reduce pain experienced by patient 12. However, the invention is not limited to systems used for delivery of SCS therapy or, for that matter, to any particular type of electrical stimulation. Other embodiments may deliver other types of neurostimulation therapy, such as cortical stimulation, deep brain stimulation, peripheral nerve stimulation, facial or cranial nerve stimulation, or vagal nerve stimulation. Further, other embodiments may deliver other kinds of electrical stimulation, such as cardiac, gastric, pelvic, muscular, or functional stimulation. Although an IMD 14 is described for purposes of illustration, various embodiments of this disclosure also may be applicable to external stimulators that deliver stimulation to internal or external locations via implanted or external electrodes.

IMD 14 delivers stimulation therapy to patient 12 according to one or more stimulation programs. A stimulation program may specify an electrode configuration and values for a number of parameters associated with stimulation delivered via the electrode configuration. The parameters may include stimulation pulse voltage or current amplitudes, pulse widths, pulse rates, and other appropriate parameters such as duration or duty cycle. Leads 16 each include one or more electrodes (not shown in FIG. 1). The program further specifies an electrode configuration in terms of electrodes that have been selected to deliver stimulation according to the program, and the polarities of the selected electrodes. Any combination of electrodes may function at any given time, including zero electrodes or all electrodes.

IMD 14 may deliver stimulation to patient 12 according to a plurality of programs at different times for a single symptom. For example, in embodiments in which IMD 14 delivers SCS therapy, the IMD may deliver stimulation intended to address leg pain according to a number of leg pain programs. Each of the leg pain programs may have different program parameters.

The different programs may be selected or tailored to be efficacious during particular times of day, or when patient 12 is in certain positions or engaged in certain activities. For example, IMD 14 may deliver neurostimulation therapy to patient 12 according to a first leg pain program using a first electrode configuration when patient 12 is lying down and deliver neurostimulation therapy to patient 12 according to a second leg pain program via a second electrode configuration when patient 12 is standing. In some embodiments, patient 12 may use programmer 20 to select from among the different programs. In other embodiments, IMD 14 may automatically select from among the different programs based on a schedule, or the output of sensors that indicate the activity or posture of patient 12, such as accelerometers or a gyroscope.

In some embodiments, IMD 14 may deliver stimulation according to a group of two or more programs at substantially the same time. Each program may address a different symptom, or programs may combine to more fully address a single symptom. IMD 14 may deliver the programs of a group at substantially the same time by, for example, alternating delivery of stimulation according to the programs of the group. Patient 12 may use programmer 20 to select from among the different program groups, or IMD 14 may automatically select from among the different programs based on a schedule, or the output of sensors that indicate the activity or posture of patient 12.

The selection of electrodes, i.e., the electrode configuration of a stimulation program, plays a large part in determining which tissues are stimulated and, therefore, which physiological effects are perceived as a result of the stimulation. Slight changes in electrode configuration may create a significant change to the efficacy or side effects associated with the therapy. Stimulation voltage or current amplitude determines the intensity and the extent of those effects. Accordingly, electrode configuration and stimulation amplitude settings may be highly related. A comfortable stimulation amplitude for one electrode configuration might be uncomfortable or imperceptible for a second electrode configuration.

Programmer 20 may allow a user to create stimulation programs for controlling delivery of stimulation by IMD 14. IMD 14 and leads 16 may provide thousands or millions of possible combinations of stimulation parameter settings. For example, a plurality of electrodes may provide numerous distinct electrode configuration possibilities. It would be an extraordinarily time consuming procedure to manually evaluate each possible electrode configuration. Further, existing stimulation systems require a clinician, using a more fully-featured clinician programming device, to play a significant role in aiding patient 12 in finding an electrode configuration that treats the patient's symptoms effectively.

According to various embodiments of the invention, programmer 20 may employ a variety of techniques to aid user in more quickly and easily identifying efficacious stimulation programs. In some embodiments, the techniques allow patient 12 to identify efficacious stimulation programs with minimal or no clinician supervision, but may also allow a clinician to identify programs for the patient. The techniques may be employed in a clinic during an office visit, or at any other time, including when patient 12 is at home. The techniques may be provided by external programmer 20, which may be a generally more fully-featured clinician programming device, or a generally less fully-featured patient programming device. Although described herein primarily with reference to external programmer 20, techniques according to the invention may alternatively be provided by IMD 14, either alone, or in combination with the programmer. The techniques may be employed during an initial programming session for patient 12, or throughout the useful lifetime of stimulation system 10, as the patient's stimulation needs change.

According to some embodiments, programmer 20 provides a user interface (not shown in FIG. 1) through which a user selects an existing program as a starting point for identification of additional programs. The selected program may be referred to as a "parent" program. Programmer 20 generates other similar programs, which may be referred to as "child" programs, from the parent program. Programmer 20 may test the child programs by directing IMD 14 to deliver stimulation according to the child programs.

The child programs will generally be similar to the parent program, but may provide more, less, or different efficacy than the parent program. Generation and testing of child programs may allow a user to "fine tune" a generally efficacious parent program, which may have been identified using different techniques. The child programs may include one or more programs that are more efficacious than the parent program, allow symptoms of the patient to be more completely addressed when combined with the parent program, or more effectively address a symptom of the patient, which may otherwise be addressed by the parent program, during particular postures, activities, or times of day. A child program may be selected as final program for long-term programming of IMD 14, or as starting points for generating further generations of child programs.

External programmer 20 may generate child programs by applying a plurality of rules, i.e., a set of rules, to the parent program. Typically, one rule from the set of rules may be applied to the parent program to generate one child program. The child program is, therefore, a slight variation of the parent program.

Each child program may be a variation of the parent based on a modification of the electrode configuration of the parent according to one of the rules. Each of the rules may define a respective electrode configuration modification based on, as examples, the proximity of active electrodes to each other, the proximity of inactive electrodes to active electrodes, or the number of active electrodes. In general, the rules include at least one of adding an active electrode, removing an active electrode, or changing the location of an active electrode. For example, a rule may specify removal of a cathode that is proximate or adjacent to another cathode, or removal of an anode if there is more than one anode. As other examples, a rule may specify adding an anode or cathode near an existing cathode, or adding an anode near an existing anode. As a further example, a rule may specify moving an anode to a proximate or adjacent inactive electrode. Some of the rules may specify more than one modification, e.g., more than one addition, removal, or movement of an active electrode. As used herein with respect to electrodes, the terms "adding," "removing" or "moving" refer to selection and/or de-selection of electrodes, i.e., turning on and/or turning off delivery of stimulation via electrodes, to achieve an addition, removal or movement of an active electrode with an array of available implanted electrodes.

In some embodiments, programmer 20 may apply the rules to one or more of the child programs to generate second generation child programs, to one or more of the second generation child programs to generate third generation child programs, and so on. In this manner, such embodiments may generate Nth generation child programs as desired by a user. Since the parent program was at least somewhat effective for stimulation therapy, the child programs may offer a more effective stimulation therapy. In the case where patient 12 finds a child program that delivers better stimulation therapy than the parent program, patient 12 may select the child program and generate another generation of child programs to perhaps find an even more efficacious program.

In general, higher generation programs, e.g., higher value of "N," will be less similar to a parent program than lower generation programs. A user may provide programmer 20 with an indication of a degree of program similarity, and programmer 20 may determine how many generations to generate and which generation to present to the user based on the requested degree of program similarity. In some embodiments, programmer 20 may select which rules to apply to programs based on user input.

For example, patient 12 may currently use a program that is very effective is treating the patient's condition. Patient 12 may instruct programmer 20 to generate similar programs to fine tune the effective program. Alternatively, patient 12 may only have a program that is marginally effective. In this case, patient 12 may instruct programmer 20 to generate programs that are more different than the selected parent program. In the latter case, programmer 20 may use only certain rules in the set of rules, or generate a fourth generation of child programs, for example. This method may decrease the time or iterations needed to identify efficacious child programs.

Programmer 20 may present child programs from one or more selected generations to the user as a list or sequence. In some cases, a child program may be a duplicate of another child program or the parent program. Duplicate child programs that were generated may be culled, i.e. deleted or not presented by programmer 20 as part of the list or sequence. Further, in embodiments in which programmer 20 stores information regarding programs presented to the patient in previous programming sessions, or is able to access information regarding programs tried by the patient outside of the clinic, programmer 20 may similarly cull newly generated child programs that duplicate such previously tried programs.

In some embodiments, programmer 20 may present a user interface that allows the user to scroll through the sequence, and select according to which of the child programs in the sequence IMD 14 will deliver stimulation. In other embodiments, programmer 20 may automatically scroll through the sequence, and control the IMD to deliver stimulation according to each of the child programs. In either case, the user may be provided with an interface to control the direction or speed of scrolling.

For example, the user may control the sequence of child programs evaluated using a time-domain metaphor, such as that found within compact disk players, digital video disk players, or audio or video tape players. For example, in some embodiments, programmer 20 may provide input controls similar to play, stop, pause, rewind, and fast forward. These controls may permit the user to navigate a list or sequence of child programs.

Additionally, programmer 20 may provide the user with the ability to control the overall intensity of the stimulations. Programmer 20 may, for example, include an input mechanism that allows the user to increase or decrease the intensity, or amplitude, of the stimulations to maintain comfortable sensations while evaluating stimulation programs. Further, in some embodiments, programmer 20 may automatically determine an initial amplitude for a child program based on the final amplitude of another child program or a parent program.

For example, when scrolling through child programs, patient 12 or a clinician may select one of the child programs, and control IMD 14 to deliver stimulation according to the selected program. The patient or clinician may adjust the amplitude of the selected program from substantially zero to a desired level. However, adjusting the amplitude of each newly selected child program from substantially zero to a desired amplitude may be tedious and time consuming.

Because the parent and child programs are generally similar, programmer 20 may automatically determine an initial amplitude of a newly selected program based on the final amplitude after adjustment for the parent program or one of the previously selected child programs. For example, programmer 20 may determine an initial amplitude of a newly selected child program based on the final amplitude of a previously selected child program. The initial amplitude for a newly selected program may be, as examples, a predetermined percentage of the final amplitude of another program, or a predetermined percentage of a mean or median of final amplitudes of a number of previous programs.

In some embodiments, the user may identify perception and/or comfort thresholds for a program. In such embodiments, programmer 20 may determine an initial amplitude for a current program based on perception and/or comfort amplitude thresholds determined for one or more previous programs. A perception threshold for a program may be an amplitude at which patient 12 first perceives the stimulation delivered by IMD 14 according to the program. A comfort threshold may be an amplitude at which stimulation according to the program is no longer comfortable for or tolerated by patient 12.

Additionally, the manner in which an initial amplitude for a program is determined may vary depending on the degree of similarity of the program to the previous, e.g., parent, program. In other words, the manner in which the initial amplitude for a current program is determined may depend on what generation the current program is in relative to the previous program. For example, in embodiments in which an initial amplitude is determined as a percentage of a final amplitude of a previous program, the percentage may increase or decrease as the degree of similarity between the current and previous programs increases or decreases.

The automatically determined initial amplitude may be non-zero, and may be perceivable. However, the automatically determined amplitude level will generally be less than the amplitude that the patient will find most efficacious and comfortable. Accordingly, the patient or clinician may increase the amplitude to a comfort threshold for each program and identify a desired therapeutic amplitude between the automatically determined initial amplitude and the comfort threshold.

Further, as mentioned above, programmer 20 may automatically control delivery of stimulation according to each child program during scrolling. In such embodiments, programmer 20 may automatically determine an initial amplitude for child programs during scrolling based on a final amplitude of one or more previously selected child programs or the parent program. In this manner, IMD 14 may deliver stimulation substantially continuously throughout scrolling without reducing the amplitude to zero or some other likely subthreshold value between child programs. Even in embodiments in which the patient adjusts the amplitude for each program during scrolling, the automatic determination of a non-zero or non-subthreshold initial amplitude may reduce the time and difficulty associated with such adjustments.

In embodiments in which IMD 14 delivers stimulation according to program groups, programmer 20 may generate child program groups from a selected parent program group. Programmer 20 may generate child program groups in a similar manner to generation of child programs, e.g., by applying one or more rules to one or more of the constituent parent programs of the selected parent program group.

Each child program group includes one or more child programs generated by application of a rule to a parent program of the parent program group. Each child program group may also include one or more of the original parent programs from the parent program group. For example, a user may select a parent program group, and elect to generate child program groups based on only one of four programs of the parent program group. Each child program group will include one of a plurality of child programs generated based on application of one or more rules to the one program of the parent program group, as well as the other three programs, unmodified, from the parent program group.

Child programs or program groups generated by the techniques of the invention may be downloaded from programmer 20 to IMD 14 via telemetry, or may be downloaded from programmer 20 to another programmer. For example, in embodiments in which programmer 20 is a clinician programmer, child programs may be downloaded to a patient programmer. Further, as described above, programmer 20 may be a patient programmer, and may download programs to IMD 14 and/or store programs locally. Additionally, as discussed above, a memory of IMD 14 may store rules, and a processor of IMD 14 may apply the rules to generate child programs or program groups as described herein. In such embodiments, IMD 14 may interact with a user via a user interface provided by programmer 20.

Figure 2:
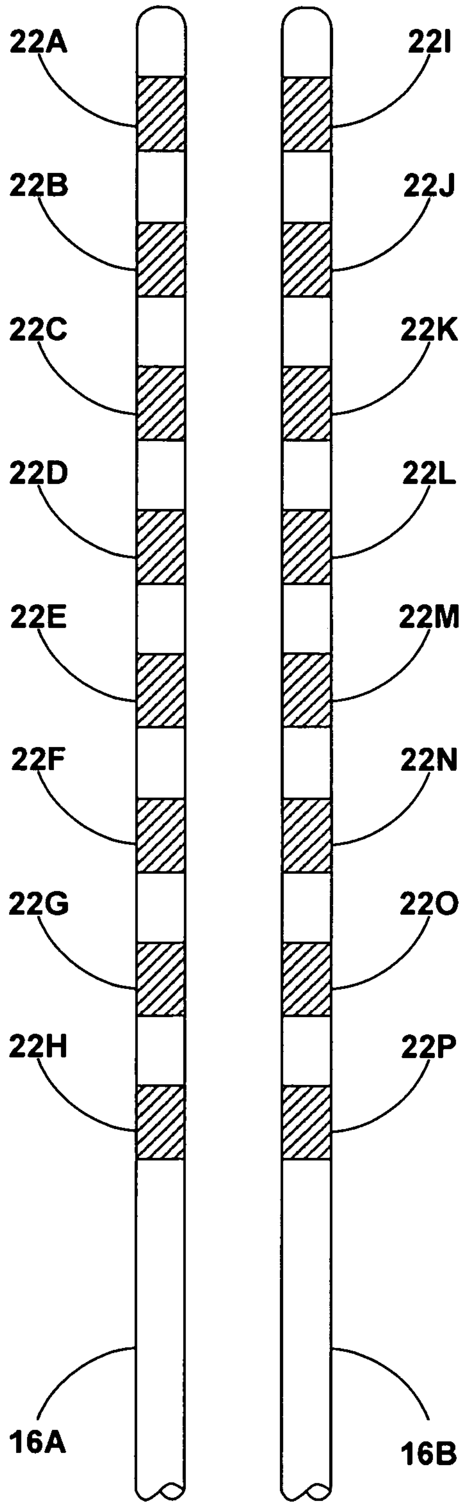
FIG. 2 is a conceptual diagram illustrating example leads with electrodes located at the distal end of each lead.

FIG. 2 is a conceptual diagram illustrating leads 16 with electrodes located at the distal end of each lead. As shown in FIG. 2, leads 16A and 16B each have eight electrodes. Lead 16A includes electrodes 22A, 22B, 22C, 22D, 22E, 22F, 22G, and 22H, while lead 16 includes electrodes 221, 22J, 22K, 22L, 22M, 22O, and 22P (collectively "electrodes 22") at their distal ends. As shown in FIG. 1, leads 16 are implanted near spinal cord 18 in order for electrodes 22 to apply electrical stimulation to the spinal cord.

During stimulation, electrodes 22 may activated according to an electrode configuration for a current stimulation program. At any given time, each of electrodes may function independently of another electrode. In other words, some electrodes may be turned on, while other electrodes 22 may be turned off. Of the electrodes 22 that are turned on, some electrodes may function as anodes while other electrodes 22 may function as cathodes. For examples, electrodes 22C and 22K may function as anodes while electrodes 22B, 22J, 22D, and 22L function as cathodes. Any combination such as this may be possible for the electrode configuration of a stimulation program. Preferably, the electrode configuration includes at least one electrode 22 functioning as an anode and at least one electrode 22 functioning as a cathode.

Electrodes 22 are described herein with reference to the overall lead configuration and structure shown in FIG. 2. However, leads 16 may not be straight leads with electrodes 22 lined up along each lead. Leads 16 may be curved or bent to produce a different shape. A different shape may be desirable for implantation at alternate anatomical sites within patient 12. For example, lead 16A may be curved in a semicircle in order for electrodes 22 to be disposed adjacent to a peripheral nerve. Alternatively, lead 16B may be bent to form an "S" shape which may be desirable to dispose electrodes 22 adjacent to a muscle needing stimulation therapy. In other embodiments, lead 16A or lead 16B may include a three-dimensional structure which houses electrodes 22 or 24, respectively. For example, electrodes 22 may be disposed in a two or three dimensional array across a paddle-like housing at the distal end of lead 16A. In any case, the shape, length, or other dimensions of lead 16A may not be identical to lead 16B.

In some embodiments, system 10 may only include one lead 16 or system 10 may include more than two leads 16. Alternatively, system 10 may include less or more electrodes on any number of leads implanted in patient 12. Leads 16 and electrodes 22 are provided only as examples. Additionally, electrodes 22 may be of any shape or size. Electrodes 22 are shown to be cylindrical in shape, but other electrode shapes, such as single sided circle electrodes may be implemented.

An electrode configuration of a stimulation program may define a spatial arrangement of active electrodes that may be beneficial to patient 12. An electrode configuration may, but does not necessarily, include active electrodes 22 that are near or adjacent to other active electrodes. Since electrodes may be arranged in two or three dimensional arrays, the adjacent electrode may be an electrode on a different lead. Specifically, an adjacent electrode need not be the next electrode in succession along a particular lead. For example, electrodes 22C, 22K, 22L, 22M, and 22E may all be adjacent electrodes to electrode 22D. In more complex electrode arrangements, smallest distance may further define an adjacent electrode.

Figure 3:
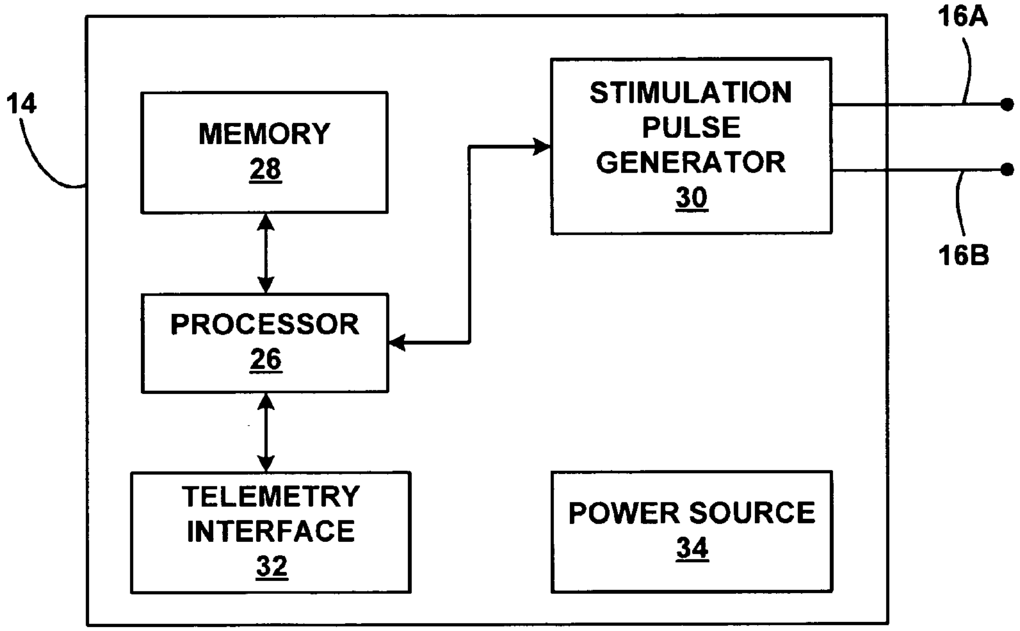
FIG. 3 is block diagram illustrating components of an example implantable medical device.

FIG. 3 is functional block diagram illustrating components of IMD 14. In the example of FIG. 3, IMD 14 includes a processor 26, memory 28, stimulation pulse generator 30, telemetry interface 32, and power source 34. As shown in FIG. 3, stimulation generator 30 is coupled to leads 16A and 16B (which include electrodes 22). Alternatively, stimulation pulse generator 30 may be coupled to a different number of leads as needed to provide stimulation therapy to patient 12.

Processor 26 controls stimulation pulse generator 30 to deliver electrical stimulation therapy according to programs stored in memory 28 and/or received from programmer 20 via telemetry interface 32. As an example, a new program received from programmer 20 may modify the electrode configuration and amplitude of stimulation. Processor 26 may communicate with stimulation pulse generator 30 to change the electrode configuration used during the therapy and modify the amplitude of stimulation. Processor 26 may then store these values in memory 28 to continue providing stimulation according to the new program. Processor 26 may stop the previous program before starting the new stimulation program as received from programmer 20. In some embodiments, amplitude of the stimulation pulses may be ramped down or ramped up as a program is being turned off or turned on. In this manner, no abrupt stimulation changes may be perceived by patient 12. A ramp up of the new program may provide patient 12 time to stop stimulation if the new program is uncomfortable or even painful.

Processor 26 may comprise any one or more of a microprocessor, digital signal processor (DSP), application specific integrated circuit (ASIC), field-programmable gate array (FPGA), or other digital logic circuitry. Memory 28 stores instructions for execution by processor 26, e.g., instructions that when executed by processor 26 cause the processor and IMD to provide the functionality ascribed to them herein, as well as stimulation programs. Memory 28 may include any one or more of a random access memory (RAM), read-only memory (ROM), electronically-erasable programmable ROM (EEPROM), flash memory, or the like.

Stimulator pulse generator 30 may provide stimulation in the form of pulses to patient 12. Stimulation parameters for each stimulation program may include electrode configuration, current or voltage amplitude, pulse width, pulse rate, or duty cycle. Other parameters may be used depending on the therapy to be provided to patient 12. Stimulation pulse generator 30 may independently utilize any electrodes 22 on leads 16A and 16B. In this manner, stimulation pulse generator 30 may be utilized to deliver stimulation via numerous different electrode configurations to provide therapy for a wide variety of patient conditions.

Telemetry interface 32 may include circuitry known in the art for facilitating wireless telemetry, e.g., via radio frequency (RF) communication or proximal inductive interaction with similar circuitry within external programmer 20. Power source 34 delivers operating power to the components of IMD 14. Power source 34 may include a battery and a power generation circuit to produce the operating power. In some embodiments, the battery may be rechargeable to allow extended operation. Recharging may be accomplished through proximal inductive interaction between an external charger and an inductive charging coil within IMD 14. In other embodiments, non-rechargeable batteries may be used. As a further alternative, an external power supply could transcutaneously power IMD 14 whenever stimulation is needed or desired.

Figure 4:
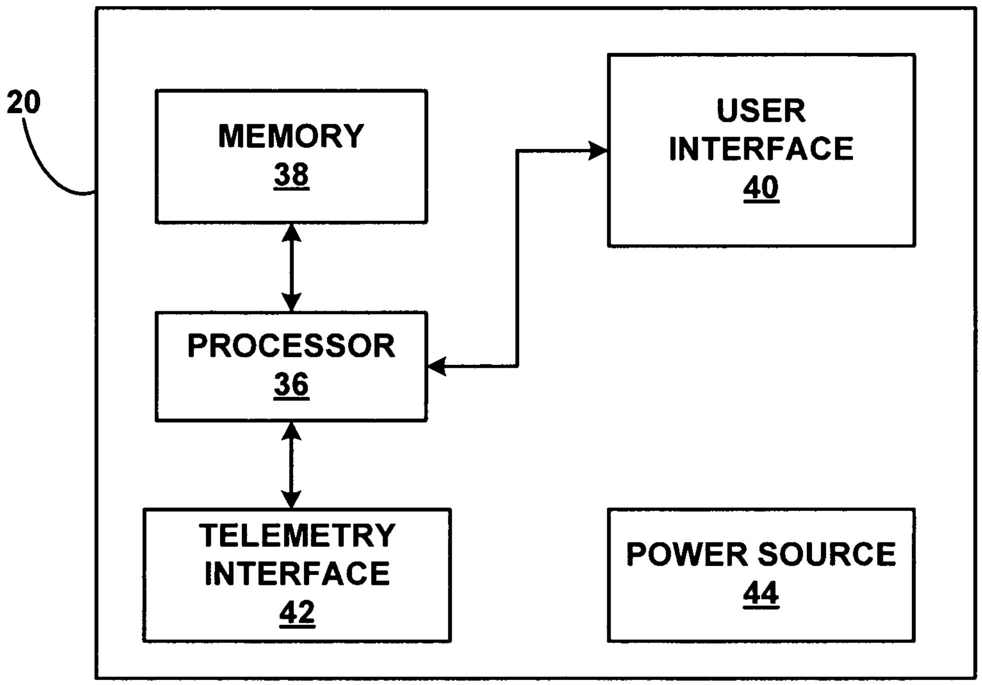
FIG. 4 is block diagram illustrating components of an example external programmer.

FIG. 4 is functional block diagram illustrating components of external programmer 20. As shown in FIG. 4, external programmer 20 includes processor 36, memory 38, user interface 40, telemetry interface 42, and power source 44. Programmer 20 may be used to select stimulation programs, generate new stimulation programs, and transmit the new programs to IMD 14. As described herein, programmer 20 may allow patient 12 or clinician to identify efficacious stimulation programs. For example, as described herein processor 36 may apply rules stored in memory 38 to a selected parent program to generate a plurality of child programs. Processor 36 may control user interface 40 to present the generated child programs to allow the user as a list or sequence, and may send child programs to IMD 14 via telemetry interface 42 to control stimulation automatically and/or as directed by the user.

Programmer 20 may be one of a patient programmer or a clinician programmer. A clinician programmer may include more functionality than the patient programmer. For example, a clinician programmer may include a more featured user interface, allow a clinician to download IMD usage and status information from IMD 14, and allow a clinician to control aspects of IMD 14 not accessible by a patient programmer.

A user, either a clinician or patient 12, may interact with processor 36 through user interface 40. User interface 40 may include a display, such as a liquid crystal display (LCD), light-emitting diode (LED) display, or other screen, to show information related to stimulation therapy, and buttons or a pad to provide input to programmer 20. Buttons may include an on/off switch, plus and minus buttons to increase and decrease parameter values or navigate through options, a select button to pick or store an input, or other buttons as needed to modify stimulation. Other input devices may be a wheel to scroll through options or a touch pad to move a pointing device on the display. In some embodiments, the display may be a touch screen that enables the user to select options directly from the display screen.

The display may be a monochrome or full color display. The display may also be backlit to enable operation in a low-light environment. Items displayed on the display may include the program currently being used, current or voltage amplitude, battery status, and program use values. Program use values may be an indication of how the program is used or is liked by patient 12. For example, the use value may be a number of hours or days the program has been used, a ranking comparing the time the program has been used in comparison to other programs, or a subjective ranking given to the program from patient 12 based upon the effectiveness of the program in treating the condition of patient 12. In addition, programmer 20 may track and store indications of programs used by or tested on patient 12. In this manner, programmer 20 may prevent programs from being repeated, e.g., prevent newly generated child programs that duplicate previously used or tested programs from being presented to the user as part of a list or sequence of child programs. This tracking may be done during only the current programming session, over several sessions, or over the duration of time that programmer 20 is used by patient 12 or a clinician that treats the patient.

During generation of child programs, the display may show other information to patient 12 or the clinician. This information may be related to the actual parameters defining the program being viewed. For example, the display may show the electrode configuration, amplitude, or other parameters associated with a program. The display may allow patient 12 or the clinician to search through other programs as well. The programs may be organized by use, efficacy, treatment area, or other metrics of program efficacy or program side effects. The programs existing prior to child program generation may be generated by a variety of means, including manual user entry or adjustment of parameters via user interface 40.

The user may select one of the programs via user interface 40 to be a parent program based on efficacy and/or side effects. Processor 36 may use a set of rules stored in memory 38 to generate child programs varying from the parent program selected by the user. As discussed above, each of the rules may define a respective electrode configuration modification based on, as examples, the proximity of active electrodes to each other, the proximity of inactive electrodes to active electrodes, or the number of active electrodes. In general, the rules include at least one of adding an active electrode, removing an active electrode, or changing the location of an active electrode. The child programs may then be evaluated by patient 12 or clinician with the goal of discovering one or more efficacious programs to treat patient 12.

Memory 38 may include instructions for operating user interface 40, telemetry interface 44 and managing power source 44. Memory 38 also includes instructions for generating child programs from a parent program. These instructions may include a set of rules that may be applied to the parent program and other guidelines and procedures for generating the child programs in response to user input. In addition, processor 36 may store all parent and child programs originally programmed or additionally generated, over one or more programming sessions, in memory 38. As discussed above, duplicate child programs that are generated according to the rules may be culled, e.g., removed from the memory.

Memory 38 may store program instructions that, when executed by processor 25, cause processor 36 and programmer 20 to provide the functionality ascribed to them herein. Memory 38 may include any one or more of a random access memory (RAM), read-only memory (ROM), electronically-erasable programmable ROM (EEPROM), flash memory, or the like. Processor 36 may comprise any one or more of a microprocessor, digital signal processor (DSP), application specific integrated circuit (ASIC), field-programmable gate array (FPGA), or other digital logic circuitry.

Wireless telemetry in programmer 20 may be accomplished by radio frequency (RF) communication or proximal inductive interaction of external programmer 20 with IMD 14. This wireless communication is possible through the use of telemetry interface 42. Accordingly, telemetry interface 42 may include circuitry known in the art for such communication.

Power source 44 delivers operating power to the components of implantable programmer 20. Power source 44 may include a battery and a power generation circuit to produce the operating power. In some embodiments, the battery may be rechargeable to allow extended operation. Recharging may be accomplished through proximal inductive interaction, or electrical contact with circuitry of a base or recharging station. In other embodiments, primary batteries may be used. In addition, programmer 20 may be directly coupled to an alternating current source.

Figure 5:
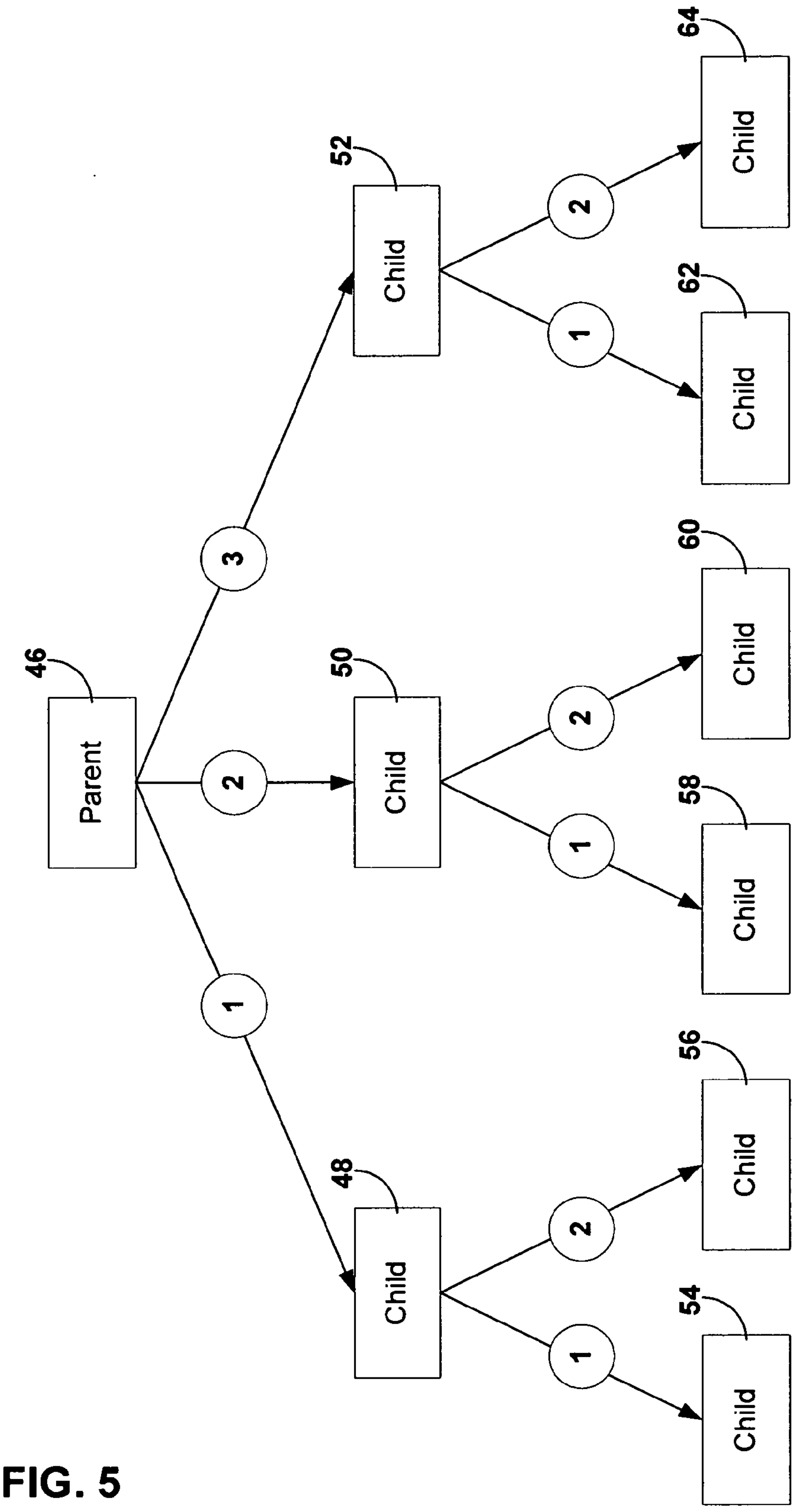
FIG. 5 is a conceptual diagram illustrating a hierarchy of child programs generated from a parent program.

FIG. 5 is a conceptual diagram illustrating the hierarchy of child programs generated from a parent program. As shown in FIG. 5, parent program 46 was selected for generation of variations of the parent program, i.e., generation of child programs. Using a set of rules, processor 36 generates each of child programs 48, 50, 52, 54, 56, 58, 60, 62, and 64 by applying a respective one rule of the set to the parent program. Child programs 48-52 are first generation programs while child programs 54-64 are second generation programs. Further $N^{th}$ generation programs may be presented to a user if a greater variation from parent program 46, e.g., less similarity between the parent and child programs, is desired.

In general, each of the rules defines a respective electrode configuration modification based on, as examples, the proximity of active electrodes to each other, the proximity of inactive electrodes to active electrodes, or the number of active electrodes. For example, each of the rules in the set may include at least one of adding an active electrode, removing an active electrode, or changing the location of an active electrode. For example, a rule may specify removal of a cathode that is proximate or adjacent to another cathode, or removal of an anode if there is more than one anode. As other examples, a rule may specify adding an anode or cathode near an existing cathode, or adding an anode near an existing anode. As a further example, a rule may specify moving an anode to a proximate or adjacent inactive electrode. Some of the rules may specify more than one modification, e.g., more than one addition, removal, or movement of an active electrode. The set of rules may be a form of “fine adjustment” for improving or generating different version of a generally desirable parent program. As mentioned above, duplicate child programs that were generated may be culled, e.g., deleted.

Processor 36 may generate as many or as few child programs as the user desires. Processor 36 may also be, but is not necessarily, limited to generating only one child program per rule. In some cases, multiple modifications of a parent program are possible based on the definition provided by one rule. For example, if a rule requires adding an anode adjacent to an existing cathode, a number of child programs may be generated based on that rule and the number of unused adjacent electrodes in the parent program.

Additionally, not all rules in the rule set may be applied to parent program 46. For example, processor 36 may only use three of ten rules in a rule set to generate child programs. Processor 36 may select the three rules based upon a user input, past success from using these three rules, or random selection. Processor 36 may store an indication which rules have been used in order to try different rules if the child programs were not successful in identifying efficacious child programs, or to try the same or similar rules if efficacious programs were identified.

As an example, an exemplary rule set including eight rules is presented to modify an electrode configuration. Each rule of the rule set describes one way in which to slightly modify the electrode configuration, and they may be used in any order. Each electrode may be a cathode or an anode, which may change the therapeutic value of the electrode combination. The example rules are:

1. Remove a cathode if it is adjacent to another existing cathode.
2. Remove an anode if there is more than one anode.
3. Add an anode adjacent to an existing cathode.
4. Add an anode adjacent to an existing cathode, and remove an anode if there is more than one anode.
5. Add an anode adjacent to an existing cathode, and add another anode adjacent to an existing cathode.
6. Move an anode to an adjacent electrode.
7. Add a cathode adjacent to an existing cathode.
8. Add an anode adjacent to an existing anode.

As can be seen, each rule of the example set defines a respective electrode configuration modification based on the proximity of active electrodes to each other, the proximity of inactive electrodes to active electrodes, or the number of active electrodes. In general, the example rule set uses electrode proximity as a way to slightly vary electrode configuration. Shifting cathodes and anodes to slightly different places may improve stimulation therapy. In some cases, one rule may always be more clinically relevant. If this is the case, weighting the clinically relevant rule may improve identification of efficacious stimulation programs. Weighting a rule may mean that each rule applied by processor 36 is a multi-step rule, or essentially each child program would be a second generation program. For example, if rule 7 was the most clinically relevant rule, each new child program would be created with a combination of rule 7 and another one of the rules of the example set.

In the example of FIG. 5, parent program 46 has been selected as an efficacious program. Only three rules from a set of rules have been chosen to be applied to parent program 46 for the purpose of generating child programs. Rule 1 is applied to generate child program 48 from parent program 46. Next, child program 50 is generated using rule 2 and child program 52 is generated using rule 3. In this case, child programs 48-52 may be, but need not be, the only unique child programs that can be generated using rules 1, 2, and 3. Second generation child programs may also generated. Rules 1 and 2 are applied to child programs 48, 50, and 52. Unique child programs 54, 56, 58, 60, 62, and 64 are the resulting child programs.

Once all nine child programs 48-64 are generated, they are presented to patient 12, e.g., in the order in which they were generated. In other embodiments, more or less child programs may be generated based upon user input or some other criteria. In addition, child programs may be presented in a different order than the order in which they were generated. For example, child programs may be presented to patient 12 in a random order. In other embodiments, parent program 46 may also be included when presenting programs to patient 12 for evaluation. If the generated child programs are not efficacious or do not provide better therapy than the parent program, the user may again direct processor 36 to generate child programs from parent program 46. Based on user input received via user interface 40, processor 36 may apply different rules from the set of rules or generate and present a different generation of child programs. In some embodiments, as discussed above, if any of child programs 48-64 were duplicates of each other or parent program 46, they may be culled from a listing or other presentation of the child programs.

Figure 6:
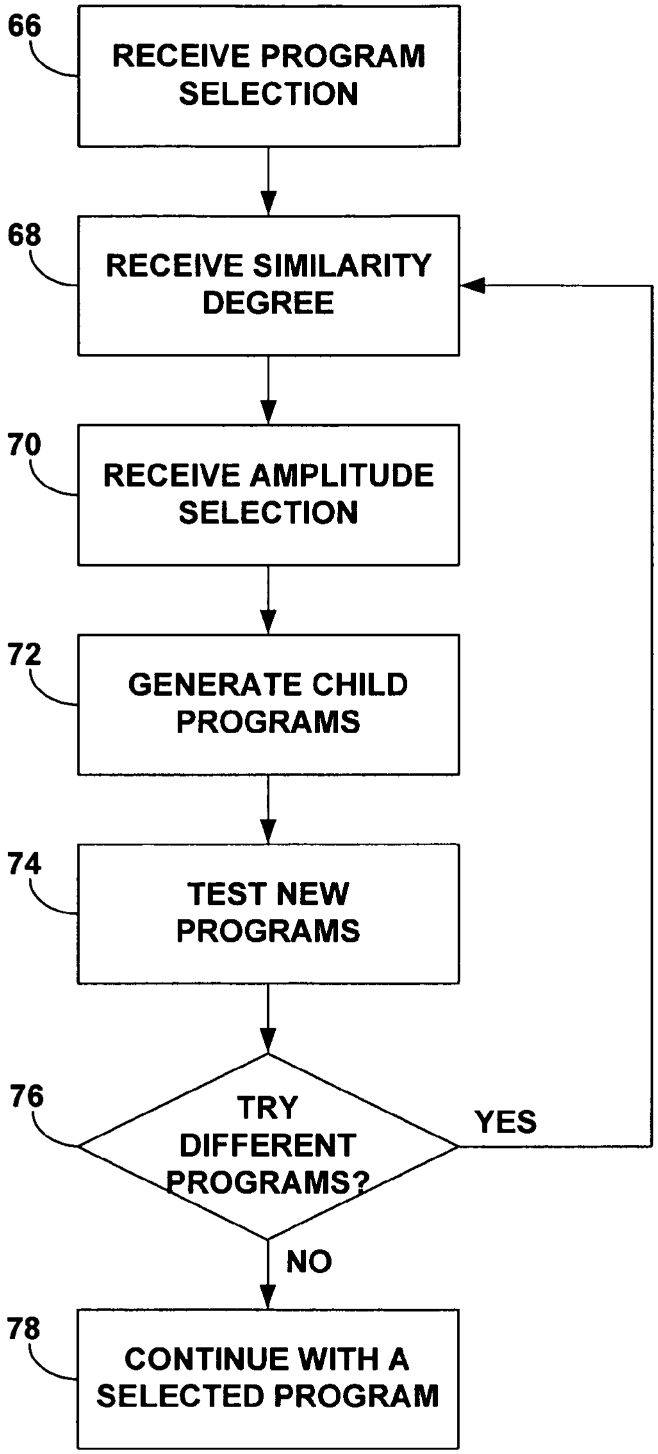
FIG. 6 is a flow diagram illustrating an example technique for generating child programs from a selected parent program.

FIG. 6 is a flow diagram illustrating an example technique for generating child programs from a selected parent program, which may be employed by processor 36 of programmer 20. In the example of FIG. 6, the user may be a clinician or patient 12. According to the example technique, processor 36 receives user selection of a parent program via user interface (66). The user may select the parent program from a list of programs generated or determined by any means, or may select the parent program by manually entering stimulation parameters for the parent programs. The user has an option to determine how similar, or different, the child programs should be in relation to the parent program. Processor 36 receives a program similarity indication from the user that guides processor 36 in generating appropriate child programs (68).

Once the similarity is selected, the user may select a starting amplitude default (70). The starting amplitude default may be an absolute amplitude value. Further, in some embodiments, as described above, processor 36 may automatically determine a non-zero starting amplitude for a child program based on the amplitude of another child program or a parent program. In such embodiments, the selected starting amplitude default may be a percentage of amplitude of the parent program or one or more previous child programs. For example, if the parent program has an amplitude of 5.0 Volts, processor 36 may automatically determine the starting amplitude for each child program to be eighty percent of the parent program amplitude, or 4.0 Volts. This default may prohibit patient 12 from experiencing painful stimulation when trying new stimulation programs, without requiring adjustment of the amplitude of each child program from zero when evaluated. In some embodiments, the starting amplitude default may not be changed by the user, and may be permanently set to a value such as eighty percent. Further, in some embodiments, the percentage may be automatically adjusted based on the degree of similarity, e.g., generation, of the child program relative to the parent, as discussed above.

Processor 36 then creates the new child programs as indicated by the user (72). Once the child programs are generated, patient 12 may test each of the new child programs (74). Over a given time period, patient 12 may test each child program. This time period may be hours, days, or months. If patient 12 desires to try different programs (76), the process may repeat with selecting a similarity variable (68). If patient 12 likes a current program, IMD 14 may continue providing therapy with a selected program (78).

In some embodiments, the user may further define the method for generating child programs. In other embodiments, processor 36 may automatically generate the child programs without any input that affects the use of the rule set or amplitude of the child programs. In addition, patient 12 or clinician may utilize this technique at anytime throughout the useful life of stimulation system 10.

Figure 7A:
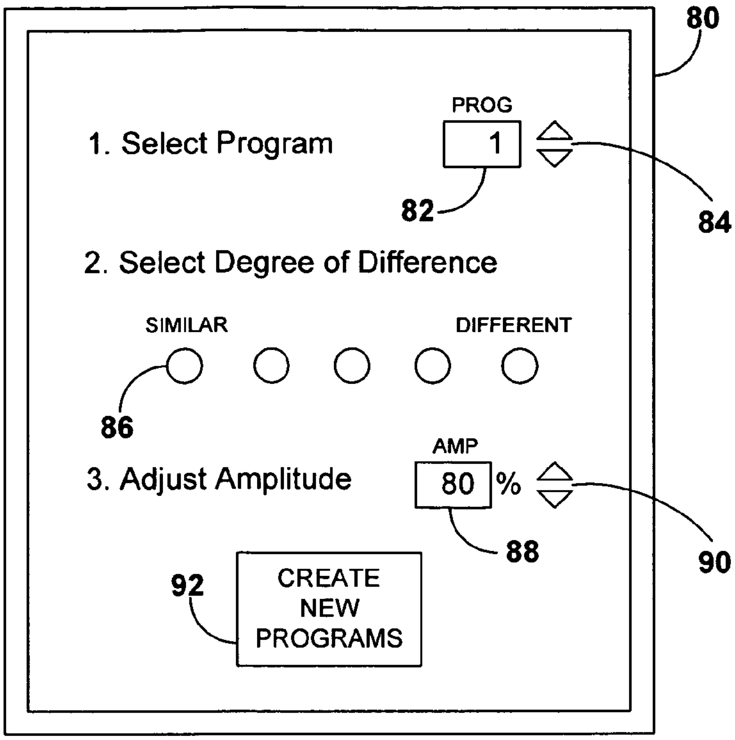
FIGS. 7A and 7B are conceptual diagrams of example user interfaces used to create child programs from a selected parent program.
Figure 7B:
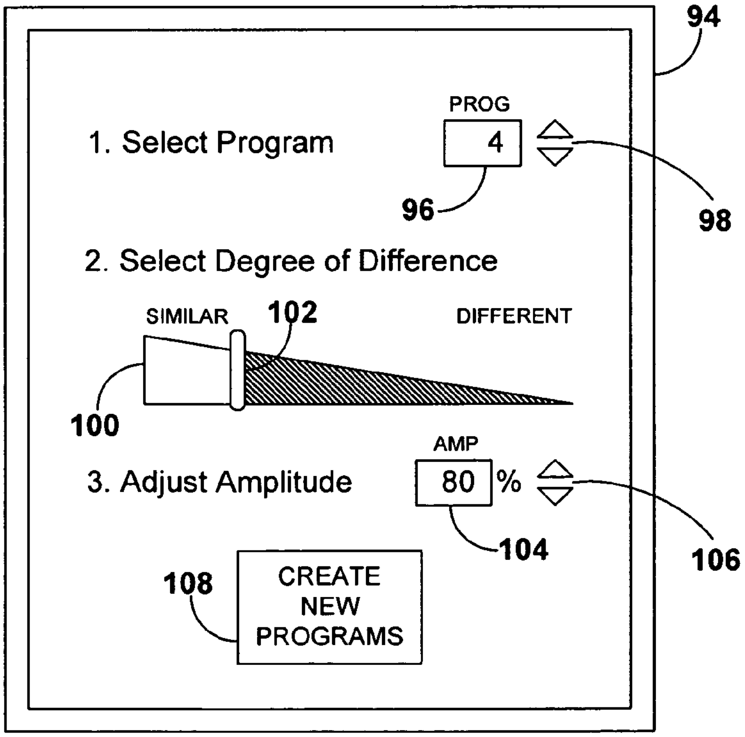

FIGS. 7A and 7B are conceptual diagrams of exemplary graphical user interfaces (GUIs) used to create child programs from a selected parent program. Both graphical user interfaces may be provided by processor 36 via user interface 40 of external programmer 20, e.g., a display of the user interface. In the example of FIG. 7A, GUI 80 is a touch screen interface. Program viewer 82 displays an identification number of the selected parent program while arrows 84 allow the user to select the number of any program stored in programmer 20. Buttons 86 allow the user to determine the similarity of the child programs to the parent program. Amplitude viewer 88 displays the amplitude percentage for the programs to be generated in relation to the amplitude of the parent program, and arrows 90 allow the user to change the percentage. Button 92 directs programmer 20 to create new child programs.

In some embodiments, the user may select the parent program through a different method than identifying the number of the program. For example, user interface 80 may provide a name or graphic icon related to the program. Alternatively, the programs may be presented based upon how often they have been used. For example, program 1 may be the program used most often, and program 10 may be the program used least often.

Selecting the variability of child programs may be done using buttons 86. The "Degree of Difference" may indicate how similar child programs are to the parent program. Based on selection of the "similar" button, a processor may generate child programs very similar to the parent program. Based on selection of the "different" button, a processor may generate child programs significantly different than the parent program. Selection of buttons between the "similar" and "different" buttons may result in a processor generating child programs with intermediate degrees of similarity to the parent program.

For example, programmer 20 may apply certain rules to generate child programs that are similar to or different than the parent program. Alternatively, programmer 20 may generate and present a higher generation, e.g., a higher Nth generation, of child programs if the user prefers child programs that are more different than parent program relative to lower generation child programs. For example, child programs of the first generation may be generated if the user desires child programs that are relatively similar to the parent, whereas fifth generation child programs may be generated is the user desires more different child programs.

The degree of difference between generated child programs may also be controlled by a user using other interfaces. For example, the user may utilize a spatial or directional interface which determines the similarity or difference of the child program. In such an interface, the distance of "movement" from a parent program would control the degree of similarity between the parent program and child programs. Further, the direction of movement may control the aspects of the program that are different or more significantly different. The spatial or directional interface may be specifically used with respect to elements of the electrode configuration, such as negative or positive polarities.

While the user may adjust the default amplitude of child programs, the maximum amplitude may be 100 percent of the parent program. This protection may be desirable to prohibit patient 12 from enduring painful stimulation during evaluation of child programs. In other embodiments, programmer 20 may automatically adjust the amplitude of child programs based upon the generated electrode configuration or other data related to therapy of patient 12, or perception and/or comfort thresholds determined for the parent program and/or other child programs. In other embodiments, the patient may manually stop an increasing amplitude to prevent uncomfortable stimulation amplitudes.

FIG. 7B shows a GUI 94 that is similar to GUI 80 of FIG. 7A. GUI 94 includes program viewer 96, arrows 98, difference graph 100, slide bar 102, amplitude viewer 104, arrows 106, and button 108. Difference graph 100 and slide bar 102 replace buttons 86 of user interface 80. The user moves slide bar 102 to determine the "Degree of Difference" of the child programs relative to the parent program. If slide bar 102 is slid to the left, or close to the "SIMILAR" end of graph 100, a processor will generate child programs similar to the parent program. As slide bar 102 is slid to the right, or closer to the "DIFFERENT" end of graph 100, a processor will generate child programs increasingly different from the parent program. Based on the position of slide bar 102, i.e., the selected degree of difference, a processor may select rules of the rule set or generations of child programs are presented to patient 12.

Figure 8:
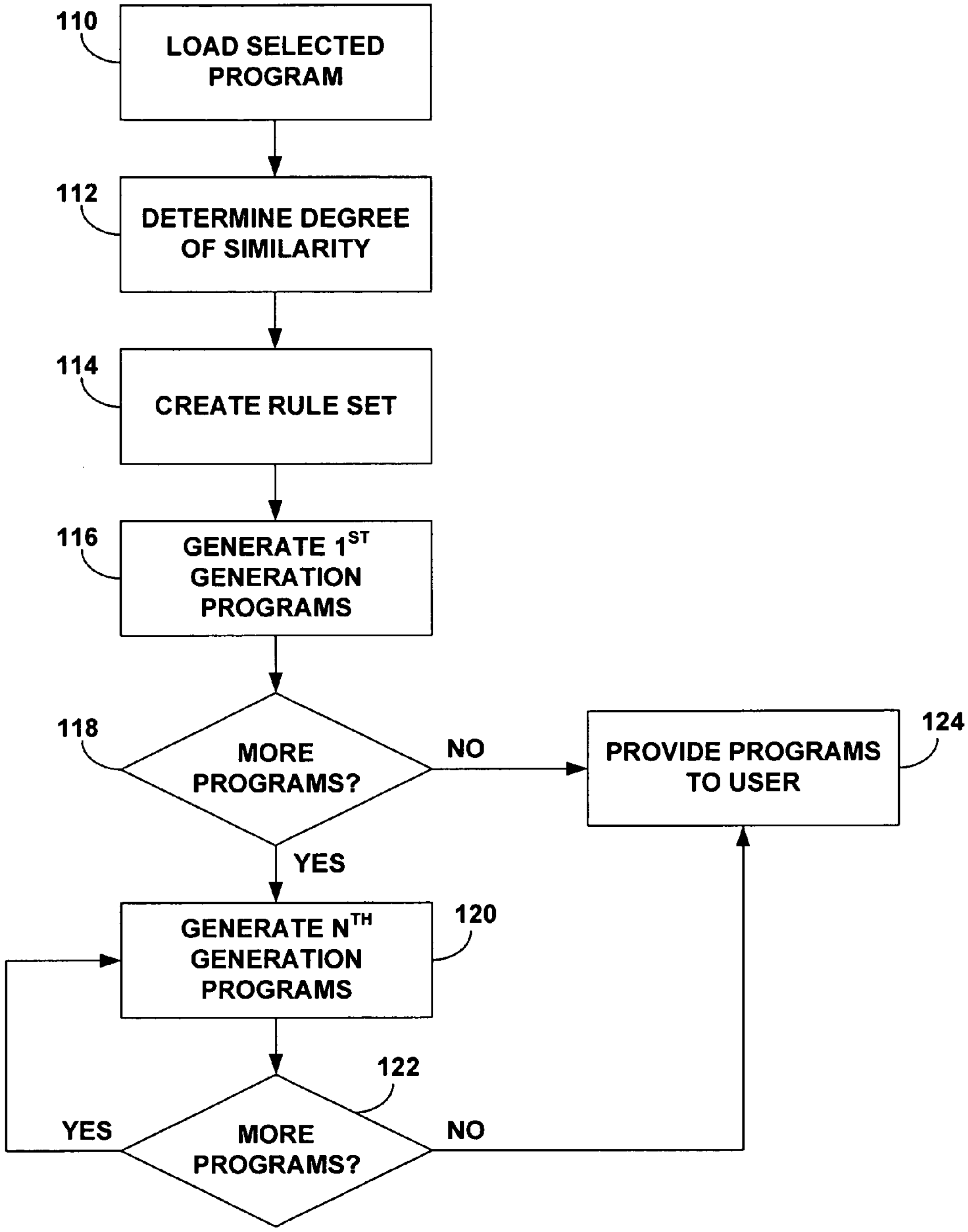
FIG. 8 is a flow diagram illustrating another example technique for generating child programs from a selected parent program.

FIG. 8 is a flow diagram illustrating another example technique for generating child programs from a selected parent program that may be employed by processor 36 of programmer 20. In the example of FIG. 8, processor 36 first loads the selected parent program from one of memories 28, 38 of IMD 14 and programmer 20 (110). Processor 36 determines the degree of similarity based upon user input (112). Processor 36 uses instructions in memory 38 to create the set of rules based upon the similarity variable (114). Rules may be taken from a preferred set of rules stored in memory 38. Processor 36 may include rules in the set of rules that will generate child programs desired by the user input. In some cases, the similarity variable may determine which generations of child programs are generated.

Processor 36 uses rules in the set of rules to generate the first generation of child programs (116). Processor 36 then determines if more child programs need to be generated (118). If no more child programs are needed, processor 36 organizes the child programs and presents them to patient 12, or another user (124). In some embodiments, processor 36 may determine if further generations of child programs are needed. If more programs are desired, processor 36 may generate another, e.g., higher N, generation of child programs (120). If more programs are desired (122), processor 36 continues to produce further generations of child programs (120).

When processor 36 has generated a desired number of programs within one or more desired generations, the processor organizes and presents the generated child programs to patient 12 or another user (124). In some embodiments, processor 26 may not present all child programs to patient 12. Processor 26 may only present the most relevant or first generated programs if a limit is set on the number of child programs that may be presented to patient 12, or may only present later generations of programs based on the selected degree of program similarity. As discussed above, processor 26 may cull duplicate programs prior to presentation.

In other cases, processor 36 may create groups of child programs organized by generation to limit the number of child programs patient 12 has to evaluate at one time. In other embodiments, processor 36 may create groups of programs for the purpose of patient 12 browsing. For example, child programs may be organized based upon the location or number of anodes in the electrode configuration, which may be more relevant to certain types of conditions. In this case, patient 12 may have groups to help organize the type of programs to evaluate. Alternatively, patient 12 may optimize an entire group of programs, instead of one program, through the optimization technique described herein.

Figure 9:
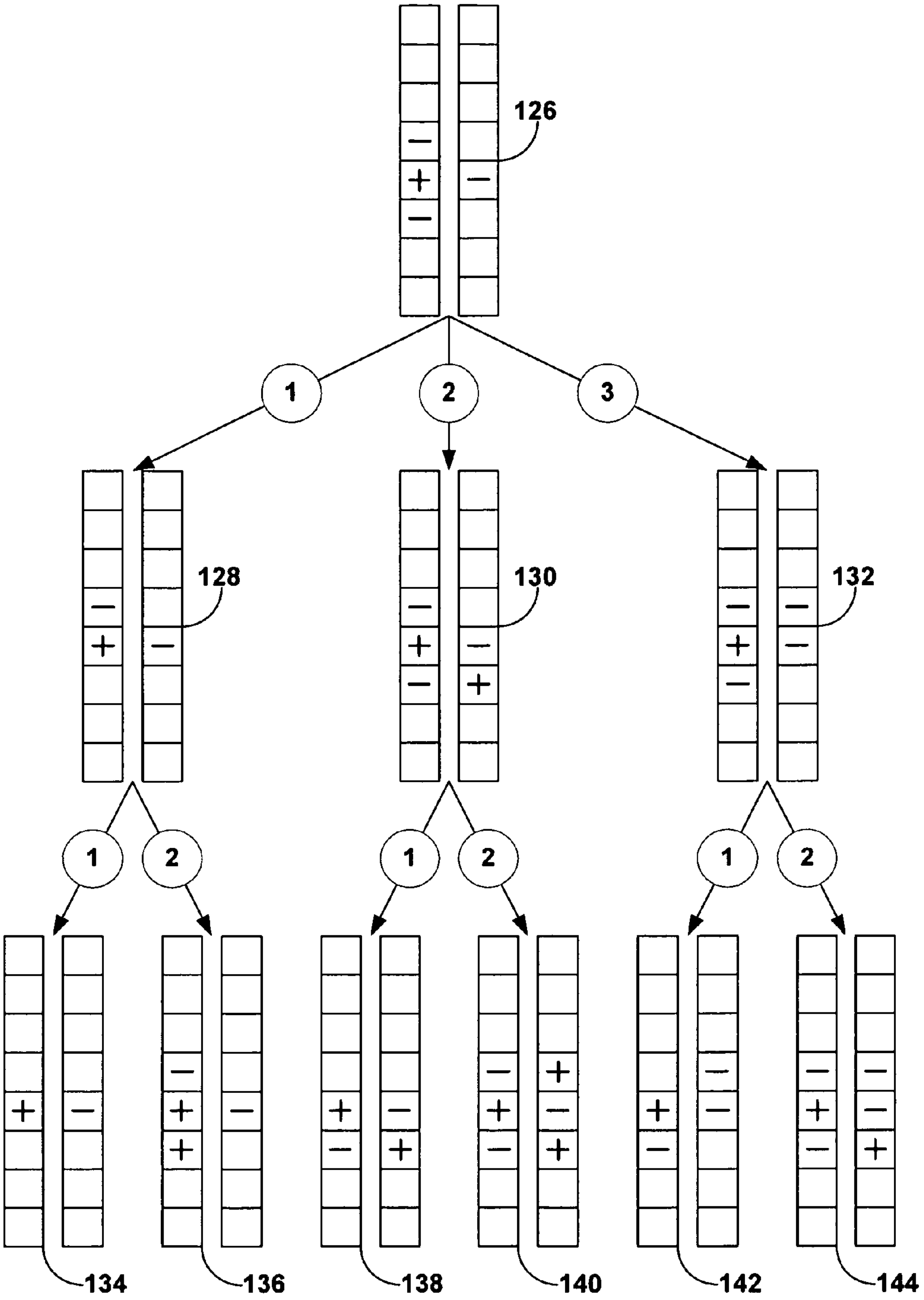
FIG. 9 is a conceptual diagram illustrating example child electrode configurations generated from a selected parent electrode configuration.

FIG. 9 is a conceptual diagram illustrating exemplary child electrode configurations generated from a selected parent electrode configuration. As shown in the example of FIG. 9, a parent program includes the illustrated parent electrode configuration 126, and each first generation child program generated from the parent program includes a respective child electrode configurations 128-132 determined based on application of a rule to the parent electrode configuration. Second generation child programs have electrode configurations 134-144 that are generated based on application of rules to the electrode configurations 128-132 of the first generation child programs. FIG. 9 may be considered to illustrate the electrode configurations of programs 46-64 shown in FIG. 5.

Electrode configuration 126 of the parent program includes four active electrodes. One electrode operates as an anode (+) and three adjacent electrodes operate as cathodes (−). All other electrodes are inactive in parent electrode configuration 126. A set of rules are applied to parent electrode configuration 126 to generate child programs with similar electrode configurations.

Rule 1 calls for processor 36 to remove a cathode if it is adjacent to another existing cathode. Processor 36 generates child electrode configuration 128 with rule 1, which now has one less cathode in the electrode configuration than parent electrode configuration 126. Child electrode configuration 130 is generated from parent electrode configuration 126 by rule 2, which calls for processor 36 to add an anode adjacent to an existing anode. Child electrode configuration 132 is generated from parent electrode configuration 126 by rule 3, which calls for processor 36 to add a cathode adjacent to an existing cathode. Child electrode configurations 128, 130, and 132 are all first generation child electrode configurations of parent electrode configuration 126. Child electrode configurations 128, 130, and 132 may provide slight changes to the perception of therapy by patient relative to parent electrode configuration 126.

Additionally, processor 36 may generate second generation child electrode configurations 134-144 from first generations child electrode configurations 128-132. Applying rule 1 and rule 2 to first generation child electrode configuration 128 results in second generation child electrode configurations 134 and 136, respectfully. Further, processor 36 may apply rules 1 and 2 to first generation child electrode configurations 130 and 132 in order for processor 36 to generate second generation child electrode configurations 138, 140, 142, and 144.

Processor 36 may organize child programs that include child electrode configurations 128-144, and present them to patient 12 or another user for evaluation. In some embodiments, a parent program including parent electrode configuration 126 may be presented to patient 12 with all child programs in order to allow patient 12 to find out if the parent program still provides more efficacious therapy than any of the generated child programs.

In the example of FIG. 9, more unique child programs may have been generated with rules 1, 2, and 3. In other words, two or more unique child programs may be generated based on application of a single rule to a parent program. In some embodiments, processor 36 may generate as many unique child programs as possible and present them all to patient 12 or another user for evaluation. In other embodiments, memory 38 may store an indication of which child programs have been generated and discarded by patient 12. In this manner, unique programs not generated during one optimization session may be generated at another time without duplicating rejected child programs.

While the set of rules provided herein describe adding or removing anodes and cathodes adjacent to other anodes or cathodes, some rules may call for adding or removing anodes or cathodes at a defined distance away from another anode or cathode. The defined distance may be equal to two electrodes from an existing anode or cathode or placing an anode or cathode as far from an existing anode or cathode as possible. Since therapy may change dramatically with these new operation electrode far from operation electrodes in a parent program, rules such as these may be reserved for when patient 12 desires different stimulation than the parent program. In addition, as the distance between anodes and cathodes increases, techniques for determining starting amplitudes may be modified to decrease likelihood of that the patient will experience uncomfortable stimulation. For example, in embodiments in which an initial amplitude is determined as a percentage of a final amplitude of a previous program, the percentage may increase or decrease as the similarity of the current and previous programs increases or decreases.

Figure 10A:
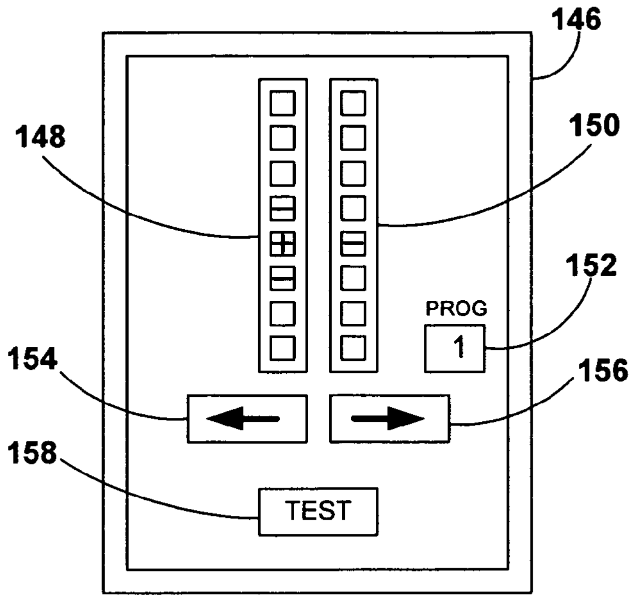
FIGS. 10A and 10B are conceptual diagrams of example user interfaces used to evaluate child programs.
Figure 10B:
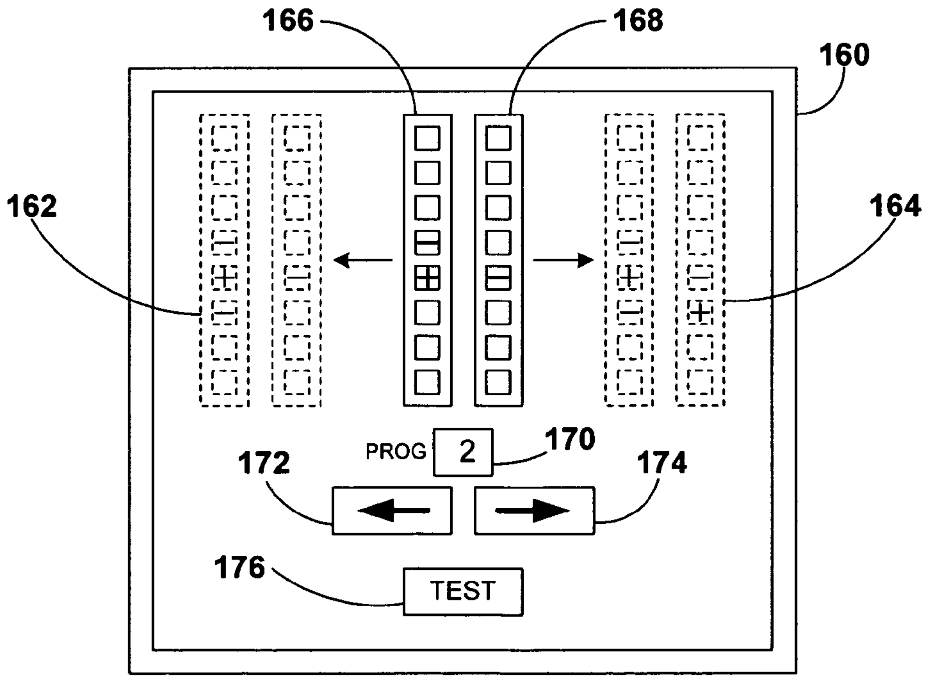

FIGS. 10A and 10B are conceptual diagrams of example GUIs used to evaluate generated child programs. The GUIs may be, for example, provided by processor 36 via a display of user interface 40 of programmer 20. As shown in FIG. 10A GUI 146 displays electrode combination 126 for program 1, which is the parent program in this example. GUI may be provided via a touch screen display, but an LCD screen and buttons may be used as well. GUI 146 includes bar 148, bar 150, program viewer 152, buttons 154, 156, and 158. Bar 148 indicates that the fourth and sixth electrodes from the top of one of the leads are cathodes, and the fifth electrode from the top is an anode. Bar 150 indicates that the fifth electrode from the top of the other lead is a cathode. Bars 148 and bar 150 show the electrode configuration for program 1, as displayed in program viewer 152.

Patient 12 may test or evaluate the therapy provided by program 1 by pressing button 158, which causes program 1 to be transmitted to IMD 14 for delivery of stimulation according to the program. Patient 12 may select another program, e.g., one of a plurality of child programs generated from the parent, by pressing button 156 to move to the next program or by pressing button 154 to move to the previously viewed program. Patient 12 may evaluate any currently-displayed program by pressing button 158. In this manner, patient 12 may evaluate a parent program, and a plurality of child programs generated from the parent program.

FIG. 10B is another example GUI for evaluating new child programs. GUI 160 is similar to GUI 146, but GUI 160 displays more than one program to patient 12 at any given time. GUI 160 includes bars 166 and 168, previous image 162, next image 164, program viewer 170, and buttons 172, 174, and 176. Program 2 is displayed by bars 166 and 168.

Patient 12 may desire to know what electrodes are operational in the current program compared to a program just evaluated or a program next to be evaluated. Previous image 162 displays the electrode configuration of program 1 to the left of the current program 2. Next image 164 displays the electrode configuration for program 3. Patient 12 may elect to evaluate program 2 by pressing button 176 and testing the therapeutic effect of the program. Patient 12 may also browse other programs by pressing button 172 to move to the previous program or pressing button 174 to move to the next program. Program viewer 170 displays the current program number.

As patient 12 experiences stimulation therapy, the patient may know that anodes or cathodes at certain locations do not provide effective therapy. Alternatively, patient 12 may have an idea of which electrode combinations are very effective in treating the condition of the patient. In these cases, user interface 160 may be appropriate to reduce the time patient 12 needs to evaluate stimulation programs and optimize the therapy.

Further, in some embodiments, as discussed above, processor 36 may automatically direct IMD 14 to deliver therapy according to the current displayed program. In such embodiments, GUIs 146 and 160 need not include test buttons 158 and 176. In some embodiments, processor 36 may automatically scroll through programs. In such embodiments, processor 36 may automatically update bars 148, 150, 166 and 168, as well as previous and next images 162 and 164 during scrolling. Processor 36 may automatically control delivery of stimulation according to a current program during scrolling. In such embodiments, GUIs 146 and 160 may still include buttons 154, 156, 172 and 174 to control the direction of scrolling. Additionally or alternatively, as discussed above, GUIs may provide a time-domain analog, such as VCR-like interface that provides stop, pause, play, fast-forward and rewind buttons, to control the direction and speed of scrolling through the programs.

As discussed above, in some embodiments a processor of a programmer may automatically determine an amplitude for a child program based on the amplitude of another child program or a parent program. For example, as illustrated and discussed with reference to FIGS. 6-8, processor 36 of programmer 20 may automatically determine the amplitude for each of a plurality of child programs to be a fixed percentage of the final adjusted or stored amplitude for the parent program. The fixed percentage may be, but need not be, selectable by patient 12.

In other embodiments, the processor may automatically determine the amplitude for a current child program to be a fixed percentage of a final adjusted amplitude of a previously evaluated child program, or an average of final adjusted amplitudes of a plurality of previously evaluated child programs. Further, amplitude adjustment according to the invention is not limited to fixed percentages. As discussed above, in other embodiments, the processor may automatically determine an amplitude for a current child program based on perception and/or comfort amplitude thresholds determined collected for previously evaluated child or parent programs. Further, as discussed above, the manner in which the initial amplitude is determined may adjusted based on the degree of similarity of the current and previous programs. For example, the fixed percentage discussed above may be adjusted based on the degree of program similarity.

Automatic determination of amplitude levels according to the invention may be advantageous in that it allows a user to scroll through and evaluate a plurality of programs without ramping up each program from a zero or other low, subthreshold amplitude value, yet is unlikely to initially deliver stimulation that a user will perceive as uncomfortable. Automatic determination of amplitude levels may be particularly advantageous in embodiments in which the processor automatically scrolls through programs and controls delivery of stimulation according to the programs, allowing relatively rapid transitions between programs while substantially constantly delivering perceivable and yet non-painful stimulation.

Figure 11:
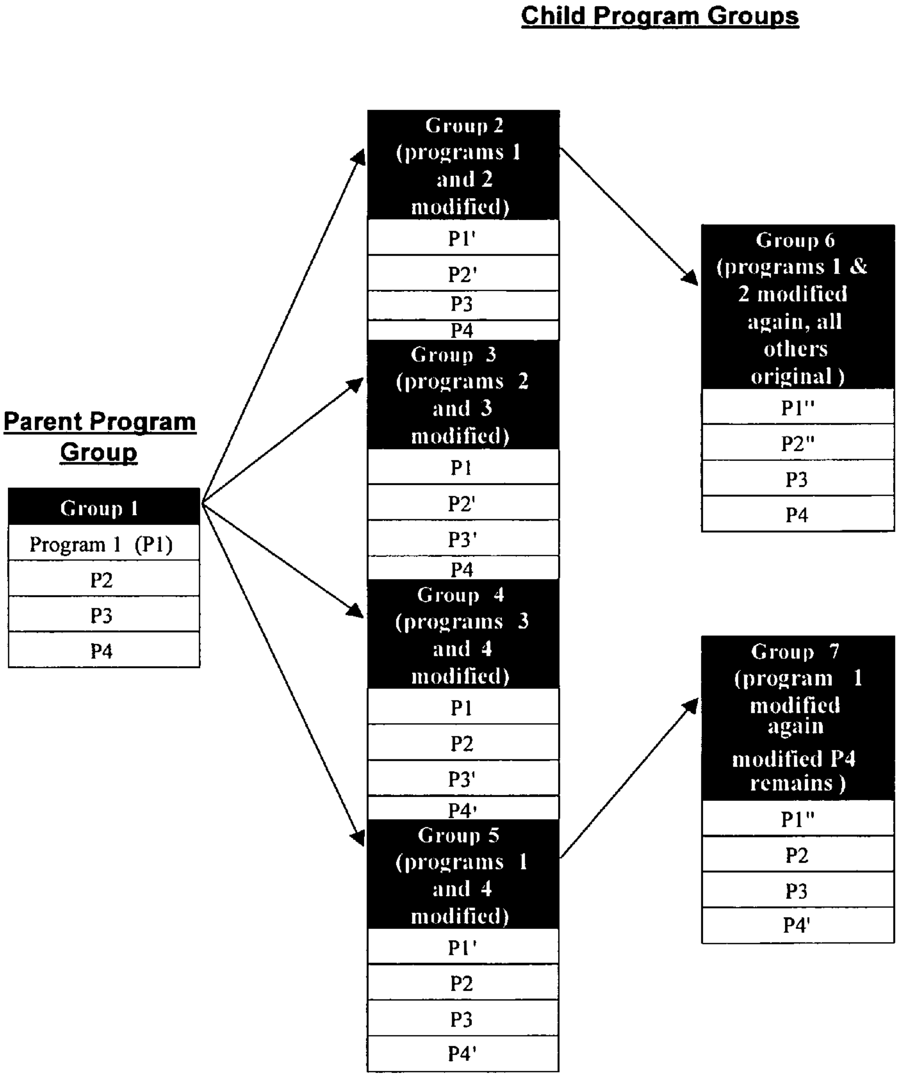
FIG. 11 is a conceptual diagram illustrating generation of child program groups from a parent program group.

FIG. 11 is a conceptual diagram illustrating generation of child program groups from a parent program group. As discussed above, in embodiments in which an IMD delivers stimulation according to program groups, a processor of a programmer or the IMD may generate child program groups from a selected parent program group. The processor may generate child program groups in a similar manner to generation of child programs, e.g., by applying one or more rules to one or more of the constituent programs of the selected parent program group.

Each child program group includes one or more child programs, and may also include one or more of the original, unmodified programs from the parent program group. For example, a user may select a parent program group, and elect to generate child program groups based on only one of four programs of the parent program group. Each child program group will include one of a plurality of child programs generated based on the one program of the parent program group, as well as the other three programs from the parent program group in their unmodified form. In this case, the different child versions of the single parent program may be derived by application of respective rules from a set of rules to the single parent program, and/or may be different "generations" of the modified program, e.g., generated by application the same or a different rule to another child version derived from the single parent program.

In the example illustrated in FIG. 11, on the other hand, each of the first generation child program groups (Groups 2-5) include two child programs and two unmodified programs from the original parent program group. Considered together, the first generation child program groups of FIG. 11 represent all possible permutations of two programs as children, e.g., modified, and two programs unmodified from the parent. Each of the child programs within the first generation child program groups of FIG. 11 have been modified "once," e.g., through application of a single rule of a set of rules by a processor, as indicated by the "single-prime" designation. The processor may apply the same rule or different rules to generate the different modified child programs in each of the child program groups.

FIG. 11 also illustrates generation of second generation child program groups by two different techniques. The child program group numbered 6 is generated by further modifying both of the previously modified child programs, as indicated by the "double-prime" designation. The child program group numbered 7 is generated by further modifying only one of the previously modified child programs. In both cases, a processor may further modify the child programs, to generate the second generation child program groups, by application of the same rule or a different rule to the electrode configuration of the previously modified child program.

In other embodiments, a processor may additionally or alternatively generate second and higher generation child program groups using techniques other than further modifying already modified child programs. For example, to generate a second or higher generation of child program group, a processor may modify a previously unmodified program within the prior generation child group, i.e., within a first generation program group to generate a second generation program group.

Table I, shown below, illustrates another example technique by which a processor may generate multiple generations of child program groups from a parent program group. In the illustrated example, the child program within each child program group that is modified varies from group to group, and each program is modified once to generate a child program group prior to a first program being modified twice to generate a child program group. The columns of Table I illustrate the resulting child program groups from application of this example technique to parent program groups with 2, 3 or 4 constituent programs, respectively. The regular script numerals in Table I represent the constituent programs of a child program group. The script numerals in Table I indicate how many times a particular program has been modified relative to the parent version of the program in the parent program group. Each child program group may be generated, i.e., each program modification may be achieved, by, for example, repeated application of a single rule, application of a respective rule, or alternating application of rules from a set of rules to an unmodified or previously modified child program.

TABLE I

| Generation of Child Program Groups Number of Programs in Parent Group | | |
|---|---|---|
| 2 | 3 | 4 |
| $1_{1}2$ | $1_{1}23$ | $1_{1}234$ |
| $12_{1}$ | $12_{1}3$ | $12_{1}34$ |

TABLE I-continued

| Generation of Child Program Groups Number of Programs in Parent Group | | |
|---|---|---|
| 2 | 3 | 4 |
| $1_2 2$ | $123_1$ | $123_1 4$ |
| $12_2$ | $1_2 23$ | $1234_1$ |
| $1_3 2$ | $12_2 3$ | $1_2 234$ |
| $12_3$ | $123_2$ | $12_2 34$ |
| $1_4 2$ | $1_3 23$ | $123_2 4$ |
| $12_4$ | $12_3 3$ | $1234_2$ |
| $1_5 2$ | $123_3$ | $1_3 234$ |

To summarize, child program groups may be generated from a parent program group in a variety of ways. In general, each child program group is the result of modification of one or more unmodified parent stimulation programs and/or further modification of one or more previously modified child programs. Each program modification may be achieved by repeated application of a single rule to the various electrode configurations, or application of a plurality of rules. In the context of generation of child program groups, user selection of a "degree of difference" may control one or more of which rules are applied to generate the child program groups, which generations of child program groups are presented to a user, how many programs are modified for generation of each new child program group, and/or how may times a particular program is modified, e.g., through application of one or more rules, to generate a child program group.

Embodiments in which child program groups are generated may be particularly useful for patients away from the clinic. Generally, such patients will be aware of stimulation at the group level, and associate desirable stimulation with a particular group. A patient may use a patient programmer to select a desirable group as a parent for refinement, or for generation of similar groups that may be more effective during particular times of day, postures or activities, through generation of child program groups. Further, a physician may use a clinician or patient programmer to generate child program groups from a generally desirable parent program group, which may have been identified based on previous patient use of the program away from the clinic, or during in clinic testing.

In either case, providing a patient with child program groups in this manner may give the patient a wider breadth of possible program solutions to explore in the comfort of his or her home. Although offering a multitude of programs would benefit the patient, creating and evaluating the programs would be a time-consuming task for the clinician in a clinic. Through automatic generation of child program groups for trial outside of the clinic, embodiments of the invention may advantageously relieve the burden of labor-intensive in-clinic generation and testing from the clinician and the patient.

Although discussed herein primarily with respect to embodiments in which a single child electrode configuration results in a single child program, the invention is not so limited. In some embodiments, single child electrode configuration will be used to create a plurality of child programs with different pulse amplitudes, pulse frequencies, pulse widths, and/or duty cycles. Further, in addition to adjusting amplitude for each program to identify a desired therapeutic amplitude, some embodiments may adjust pulse frequency or pulse width to identify desired therapeutic values for each program.

Although discussed herein primarily with reference to a programmer that communicates with an IMD, the techniques of the invention may be employed by an IMD, as discussed above. A memory of the IMD may store rules, and a processor of the IMD may apply the rules to generate child programs or program groups as described herein. In such embodiments, the IMD may interact with a user via a user interface provided by a programmer that communicates with IMD.

Further, although the invention may be especially applicable to the simulation of the spinal cord, the invention alternatively may be applied more generally to any type of stimulation delivered according to programs via a plurality of configurable electrodes. As examples, cortical brain stimulation, deep brain stimulation, sacral or pedundal nerve stimulation, or dorsal root stimulation may benefit from the search technique described herein.

Various embodiments of the described invention may include processors that are realized by microprocessors, Application-Specific Integrated Circuits (ASIC), Field-Programmable Gate Arrays (FPGA), or other equivalent integrated logic circuitry. The processor may also utilize several different types of storage methods to hold computer-readable instructions for the device operation and data storage. These memory and storage media types may include a type of hard disk, random access memory (RAM), or flash memory, e.g. CompactFlash or SmartMedia. Each storage option may be chosen depending on the embodiment of the invention. While neurostimulator 14 may contain permanent memory, external programmer 20 may contain a more portable removable memory type to enable easy data transfer or offline data analysis.

Many embodiments of the invention have been described. Various modifications may be made without departing from the scope of the claims. These and other embodiments are within the scope of the following claims.

The invention claimed is:

1. A method comprising:

selecting a parent stimulation program, the parent stimulation program including a parent electrode configuration;

receiving an indication of a degree of program similarity from a user, the indication of the degree of program similarity being indicative of how similar a plurality of child programs are to the parent stimulation program;

applying each of a plurality of rules to the parent electrode configuration, each of the rules defining a respective electrode configuration modification based on at least one of proximity of active electrodes to each other, proximity of inactive electrodes to active electrodes, or number of active electrodes, wherein at least one aspect of the application of the rules to the parent electrode configuration is selected based on the indicated degree of program similarity; and generating the plurality of child programs based on the application of the rules to the parent electrode configuration, wherein each of the child programs includes a respective child electrode configuration determined by application of one of the rules to the parent electrode configuration.

2. The method of claim 1, further comprising:

applying at least one of the rules to at least one of the child electrode configurations; and generating at least one second generation child program based on the application of the rule to the child electrode configuration, the second generation child program including a second generation child electrode configuration.

3. The method of claim 1, further comprising:

based on the degree of program similarity, applying the rules to at least one of the parent electrode configuration or at least one of the child electrode configurations to generate Nth generation child programs, wherein a lower degree of program similarity corresponds to a larger N, and wherein N is selected based on the indicated degree of program similarity, and wherein N is greater than 1.

4. The method of claim 3, further comprising presenting only generated child programs of the Nth generation.

5. The method of claim 1, further comprising presenting the child programs to a user in a sequence.

6. The method of claim 5, further comprising scrolling through the sequence of child programs.

7. The method of claim 6, further comprising providing a user interface to allow the user to control at least one of the rate or direction of scrolling through the sequence of child programs.

8. The method of claim 6, further comprising automatically delivering stimulation according to current ones of the child programs during scrolling through the sequence of child programs.

9. The method of claim 1, further comprising:

delivering stimulation according to a first one of the child programs;

receiving input from a user adjusting an amplitude of the first child program to a final value;

automatically determining an initial value for an amplitude of a second one of the child programs based on the final value of the amplitude of the first child program; and delivering stimulation according to the second child program including the determined initial value for the amplitude of the second child program.

10. The method of claim 9, wherein automatically determining an initial value comprises applying a predetermined percentage to the final value.

11. The method of claim 1, further comprising automatically determining an initial amplitude for one of the child programs based on the indicated degree of program similarity.

12. The method of claim 1, further comprising automatically determining an initial amplitude for one of the child programs based on at least one of perception or comfort thresholds for at least one of the parent program or previously delivered ones of the child programs.

13. The method of claim 1, wherein selecting a parent stimulation program comprises selecting a parent program group, the parent program group including a plurality of parent stimulation programs, and each of the parent stimulation programs including a respective one of a plurality of parent electrode configurations, wherein applying each of the plurality of rules to the parent electrode configuration comprises applying each of the plurality of rules to at least one of the parent electrode configurations, and wherein generating a plurality of child programs comprises generating a plurality of child program groups based on the application of the rules to the parent electrode configuration.

14. The method of claim 13, further comprising providing the plurality of child program groups to at least one of an implantable medical device or a patient programming device for selection by a patient and delivery of therapy to the patient.

15. The method of claim 13, wherein applying each of the plurality of rules to the parent electrode configuration comprises applying each of the plurality of rules to a number of the parent electrode configurations selected based on the indicated degree of program similarity.

16. The method of claim 1, further comprising deleting any of the plurality of child programs that are duplicates.

17. The method of claim 16, further comprising tracking program use to identify duplicates over a plurality of programming sessions.

18. The method of claim 1, wherein one of the plurality of rules comprises placing one of an anode or a cathode as far from an active electrode as possible.

19. The method of claim 1, wherein one of the plurality of rules based on a number of active electrodes comprises removal of an anode when the parent electrode configuration comprises more than one anode.

20. The method of claim 1, wherein the plurality of applied rules are selected from amongst available rules based on the indicated degree of program similarity.

21. The method of claim 1, wherein generating the plurality of child programs comprises generating a plurality of generations of child programs in response to receiving the indication of the degree of program similarity.

22. A system comprising:

a memory that stores a plurality of rules, each of the rules defining a respective electrode configuration modification based on at least one of proximity of active electrodes to each other, proximity of inactive electrodes to active electrodes, or number of active electrodes; and a processor that selects a parent stimulation program, the parent stimulation program including a parent electrode configuration, receives an indication of a degree of program similarity from a user via a user interface, the indication of the degree of program similarity being indicative of how similar a plurality of child programs are to the parent stimulation program, applies each of the plurality of rules to the parent electrode configuration, and generates the plurality of child programs based on the application of the rules to the parent electrode configuration, wherein:

at least one aspect of the application of the rules to the parent electrode configuration is selected based on the indicated degree of program similarity; and each of the child programs includes a respective child electrode configuration determined by application of one of the rules to the parent electrode configuration.

23. The system of claim 22, wherein the processor applies at least one of the rules to at least one of the child electrode configurations, and generates at least one second generation child program based on the application of the rule to the child electrode configuration, the second generation child program including a second generation child electrode configuration.

24. The system of claim 22, wherein the processor, based on the degree of program similarity, applies the rules to at least one of the parent electrode configuration or at least one of the child electrode configurations to generate Nth generation child programs, wherein a lower degree of program similarity corresponds to a larger N, and wherein N is selected based on the indicated degree of program similarity, and wherein N is greater than 1.

25. The system of claim 22, wherein the processor presents the child programs to a user in a sequence via the user interface.

26. The system of claim 25, wherein the processor scrolls through the sequence of child programs.

27. The system of claim 26, wherein the user interface allows the user to control at least one of the direction or rate of scrolling through the sequence of child programs by the processor.

28. The system of claim 26, wherein the processor automatically controls delivery of stimulation by an implantable medical device according to current ones of the child programs during scrolling through the sequence of child programs.

29. The system of claim 22, wherein the processor controls delivery of stimulation by an implantable medical device according to a first one of the child programs, receives input from a user adjusting an amplitude of the first program to a final value via the user interface, automatically determines an initial value for an amplitude of a second one of the child programs based on the final value of the amplitude of the first child program, and controls the implantable medical device to deliver stimulation according to the second child program including the determined initial value for the amplitude of the second child program.

30. The system of claim 29, wherein the processor applies a predetermined percentage to the final value in order to determine the initial value.

31. The system of claim 22, wherein the processor automatically determines an initial amplitude for one of the child programs based on at least one of perception or comfort thresholds for at least one of the parent program or previously delivered ones of the child programs.

32. The system of claim 22, wherein the processor automatically determines an initial amplitude for one of the child programs based on the similarity of the child program to the parent program.

33. The system of claim 22, wherein the processor selects a parent program group, the parent program group including a plurality of parent stimulation programs, and each of the parent stimulation programs including a respective one of a plurality of parent electrode configurations, applies each of the plurality of rules to at least one of the parent electrode configurations, and generates a plurality of child program groups based on the application of the rules to the parent electrode configuration.

34. The system of claim 33, wherein the processor provides the plurality of child program groups to at least one of an implantable medical device or a patient programming device for selection by a patient and delivery of therapy to the patient.

35. The system of claim 22, wherein the processor deletes any of the plurality of child programs that are duplicates.

36. The system of claim 35, wherein the processor tracks program use to identify duplicates over a plurality of programming sessions.

37. The system of claim 22, further comprising a clinician programming device that includes the processor, the memory, a user interface and telemetry circuitry for communication with at least one of an implantable medical device or patient programming device.

38. A computer-readable storage medium comprising instructions that cause a programmable processor to:

select a parent stimulation program, the parent stimulation program including a parent electrode configuration;

receive an indication of a degree of program similarity from a user, the indication of the degree of program similarity being indicative of how similar a plurality of child programs are to the parent stimulation program;

apply each of a plurality of rules to the parent electrode configuration, each of the rules defining a respective electrode configuration modification based on at least one of proximity of active electrodes to each other, proximity of inactive electrodes to active electrodes, or number of active electrodes, wherein at least one aspect of the application of the rules to the parent electrode configuration is selected based on the indicated degree of program similarity; and generate the plurality of child programs based on the application of the rules to the parent electrode configuration, wherein each of the child programs includes a respective child electrode configuration determined by application of one of the rules to the parent electrode configuration.

39. The computer-readable storage medium of claim 38, further comprising instructions that cause a programmable processor to:

apply at least one of the rules to at least one of the child electrode configurations; and generate at least one second generation child program based on the application of the rule to the child electrode configuration, the second generation child program including a second generation child electrode configuration.

40. The computer-readable storage medium of claim 38, further comprising instructions that cause a programmable processor to, based on the degree of program similarity, apply the rules to at least one of the parent electrode configuration or at least one of the child electrode configurations to generate Nth generation child programs, wherein a lower degree of program similarity corresponds to a larger N, and wherein N is selected based on the indicated degree of program similarity, wherein N is greater than 1.

41. The computer-readable storage medium of claim 38, further comprising instructions that cause a programmable processor to present the child programs to a user in a sequence.

42. The computer-readable storage medium of claim 41, further comprising instructions that cause a programmable processor to scroll through the sequence of child programs.

43. The computer-readable storage medium of claim 42, further comprising instructions that cause a programmable processor to provide a user interface to allow the user to control at least one of the rate or direction of scrolling through the sequence of child programs.

44. The computer-readable storage medium of claim 42, further comprising instructions that cause a programmable processor to automatically control delivery stimulation according to current ones of the child programs during scrolling through the sequence of child programs.

45. The computer-readable storage medium of claim 38, further comprising instructions that cause a programmable processor to:

control delivery of stimulation according to a first one of the child programs;

receive input from a user adjusting an amplitude of the first child program to a final value;

automatically determine an initial value for an amplitude of a second one of the child programs based on the final value of the amplitude of the first child program; and control delivery of stimulation according to the second child program including the determined initial value for the amplitude of the second child program.

46. A method comprising:

selecting a parent program group, the parent program group including a plurality of parent stimulation programs, and each of the parent stimulation programs including a respective one of a plurality of parent electrode configurations;

receiving an indication of a degree of program similarity from a user, the indication of the degree of program similarity being indicative of how similar a plurality of child programs are to the parent stimulation program;

applying a rule to each of the parent electrode configurations, the rule defining an electrode configuration modification based on at least one of proximity of active electrodes to each other, proximity of inactive electrodes to active electrodes, or number of active electrodes, wherein at least one aspect of the application of the rules to the parent electrode configuration is selected based on the indicated degree of program similarity; and generating the plurality of child program groups based on the application of the rule to the parent electrode configurations, wherein each of the child program groups includes a respective child stimulation program and corresponding child electrode configuration determined by application of the rule to the parent electrode configuration.

47. A system comprising:

a memory that stores a rule that defines an electrode configuration modification based on at least one of proximity of active electrodes to each other, proximity of inactive electrodes to active electrodes, or number of active electrodes; and a processor that selects a parent program group, the parent program group including a plurality of parent stimulation programs, and each of the parent stimulation programs including a respective one of a plurality of parent electrode configurations, receives an indication of a degree of program similarity from a user via a user interface, the indication of the degree of program similarity being indicative of how similar a plurality of child programs are to the parent stimulation program, applies the rule to each of the parent electrode configurations, and generates the plurality of child program groups based on the application of the rule to the parent electrode configurations, wherein:

at least one aspect of the application of the rules to the parent electrode configuration is selected based on the indicated degree of program similarity; and each of the child program groups includes a respective child stimulation program and corresponding child electrode configuration determined by application of the rule to the parent electrode configuration.

* * * * *

UNITED STATES PATENT AND TRADEMARK OFFICE

CERTIFICATE OF CORRECTION

PATENT NO. : 8,712,539 B2
APPLICATION NO. : 11/402657
DATED : April 29, 2014
INVENTOR(S) : Goetz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1590 days.

Signed and Sealed this
Eleventh Day of August, 2015

Michelle K. Lee
*Director of the United States Patent and Trademark Office*